(12) United States Patent
Hickman

(10) Patent No.: US 7,734,426 B2
(45) Date of Patent: Jun. 8, 2010

(54) HIGH THROUGHPUT FUNCTIONAL GENOMICS

(75) Inventor: James J. Hickman, Orlando, FL (US)

(73) Assignee: Hesperos, LLC, Pendleton, SC (US)

( * ) Notice: Subject to any disclaimer, the term of this patent is extended or adjusted under 35 U.S.C. 154(b) by 466 days.

(21) Appl. No.: 11/840,041

(22) Filed: Aug. 16, 2007

(65) Prior Publication Data

US 2008/0124789 A1 May 29, 2008

Related U.S. Application Data

(63) Continuation of application No. 09/575,377, filed on May 22, 2000, now Pat. No. 7,266,457.

(60) Provisional application No. 60/135,275, filed on May 21, 1999.

(51) Int. Cl.
G06F 19/00 (2006.01)
C12N 15/00 (2006.01)
G01N 33/53 (2006.01)
C12M 1/34 (2006.01)

(52) U.S. Cl. .................. 702/19; 435/7.1; 435/287.1; 435/325

(58) Field of Classification Search .................. None
See application file for complete search history.

(56) References Cited

U.S. PATENT DOCUMENTS

| | | | |
|---|---|---|---|
| 5,077,210 A | 12/1991 | Eigler et al. | |
| 5,223,117 A | 6/1993 | Wrighton et al. | |
| 5,324,591 A | 6/1994 | Georger, Jr. et al. | |
| 5,648,926 A | 7/1997 | Douglas et al. | |
| 5,721,131 A | 2/1998 | Rudolph et al. | |
| 5,759,846 A | 6/1998 | Stoppini et al. | |
| 5,810,725 A | 9/1998 | Sugihara et al. | |
| 5,981,268 A | 11/1999 | Kovacs et al. | |
| 6,297,025 B1 | 10/2001 | Sugihara et al. | |
| 6,377,057 B1 | 4/2002 | Borkholder | |
| 6,699,697 B2 | 3/2004 | Klemic et al. | |
| 2003/0054333 A1 | 3/2003 | Hickman et al. | |
| 2005/0227139 A1* | 10/2005 | Methfessel et al. | 429/44 |
| 2007/0060815 A1* | 3/2007 | Martin et al. | 600/372 |
| 2007/0155015 A1* | 7/2007 | Vassanelli et al. | 435/461 |

FOREIGN PATENT DOCUMENTS

| | | |
|---|---|---|
| EP | 069051 | 12/1995 |
| EP | 0823483 | 2/1998 |
| WO | WO9854294 | 12/1998 |
| WO | WO0071742 | 11/2000 |

OTHER PUBLICATIONS

Jung et al., "Cell-Based Sensor Microelectrode Array Characterised by Imaging X-Ray Photoelectron Spectroscopy, Scanning Electro Microscopy, Impedance Measurements and Extracellular Recordings" J. Vacuum Science and Technology, vol. 16, No. 3, 1998, pp. 1183-1188, Of Record.
Ambros-Ingerson et al., "Stimulation of Paleocortex Performs Hierarchical Clustering" Science, 247; 1990: 1344-48, Of Record.
Granger et al., "An Introduction to Neural and Electronic Networks" Ed's Zornetzer, S.F., Davis, L.J., and Lau, C., Academic Press, Inc., San Diego; 1991: 25-42, Of Record.
Adleman, "Molecular Computation of Solutions to Combinatorial Problems" Science, vol. 266, 1994, Of Record.
Palsson, "Bioinformation and the Creation of Biological Pathways or Genetic Circuits Using Silicon Based Models" 1997, Of Record.
Gross et al., "The Use of Neuronal Networks on Multielectrode Arrays as Biosensors" Biosens. Bioelectron., 10, 1995: 553-567; 1, Of Record.
Stenger et al., Related Articles—"Microlithographic Determination of Axonal/Dendritic Polarity in Cultured Hippocampal Neurons" J. Neurosci. Methods; Aug. 1; 82(2) 1998: 167-73, Of Record.
LeMasson et al., "Activity-Dependent Regulation of Conductances in Model Neurons" Science, 259, 1993: 1915-17, Of Record.
Marder et al., "Theory in Motion" Curr. Opin. Neurobiol.; 5, 1995: 832-40, Of Record.
Schizas, "Learning Systems in Biosignal Analysis" Biosystems; 41, 1997: 105-25, Of Record.
Hickman et al., "Toward Orthogonal Self-Assembly of Redox Active Molecules on Pt and Au: Selective Reaction of Disulfide with Au and Isonitrile with Pt" Langmuir; 8: 1992: 357, Of Record.

(Continued)

Primary Examiner—Lori A Clow
(74) Attorney, Agent, or Firm—Neifeld IP Law, PC

(57) ABSTRACT

This invention focuses on the marriage of solid-state electronics and neuronal function to create a new high-throughput electrophysiological assay to determine a compound's acute and chronic effect on cellular function. Electronics, surface chemistry, biotechnology, and fundamental neuroscience are integrated to provide an assay where the reporter element is an array of electrically active cells. This innovative technology can be applied to neurotoxicity, and to screening compounds from combinatorial chemistry, gene function analysis, and basic neuroscience applications. The system of the invention analyzes how the action potential is interrupted by drugs or toxins. Differences in the action potentials are due to individual toxins acting on different biochemical pathways, which in turn affects different ion channels, thereby changing the peak shape of the action potential differently for each toxin. Algorithms to analyze the action potential peak shape differences are used to indicate the pathway(s) affected by the presence of a new drug or compound; from that, aspects of its function in that cell are deduced. This observation can be exploited to determine the functional category of biochemical action of an unknown compound. An important aspect of the invention is surface chemistry that permits establishment of a high impedance seal between cell and a metal microelectrode. This seal recreates the interface that enables functional patch-clamp electrophysiology with glass micropipettes, and allows extracellular electrophysiology on a microelectrode array. Thus, the invention teaches the feasibility of using living cells as diagnostics for high throughput real-time assays of cell function.

25 Claims, 11 Drawing Sheets

OTHER PUBLICATIONS

Apr. 21, 1995, Schaffner et al., "Investigation of the Factors Necessary for Growth of Hippocampal Neurons in a Defined System" Journal of Neuroscience Methods 62 (1995) 111-119, Of Record.

Riley, "Functions of Gene Products of *Escherichia coli*" Microbiol. Rev.; 57; 1993: 862-952, Of Record.

Freshney, "Culture of Animal Cells. A Manual of Basic Techniques" 4th Ed., Wiley, John & sons, Mar. 2000; Abstract, Of Record.

Fromherz et al., "A Neuron-Silicon Junction: A Retzius Cell of the Leech on an Insulated-Gate Filed-Effect Transistor" Science; 252; 1991: 1290-93, Of Record.

Becerril et al., "Toxins and Genes Isolated from Scorpions of the genus Tityus" Toxicon, 35, 1997: 821-35, Of Record.

Brazil et al., "Toxins as Tools in the Study of Sodium Channel Distribution in the Muscle Fibre Membrane" Toxicon, 31; 1993: 1085-98, Of Record.

Cantiello, "Role of the Actin Cytoskeleton on Epithelial $Na^+$ Channel Regulation" Kidney Int.; 48, 1995: 970-984, Of Record.

Cassola et al., "Use of Neurotoxins to Study $Ca^{2+}$ Channel Functions" Braz. J. Med. Biol. Res., 29; 1996: 1759-63, Of Record.

Catterall et al., "Molecular Properties of the Sodium Channel: a Receptor for Multiple Neurotoxins" Bull. Soc. Pathol. Exot, 85 (5 Pt 2); 1992: 481-85, Of Record.

Childres et al., "Role of Cyclic AMP in the Actions of the Cannabinoid Receptors" Biochem. Pharmacol., 52, 1996: 819-27, Of Record.

Cowan et al., "Hypothesis for Synergistic Toxicity of Organophosphorus Poisoning-Induced Cholinergic Crises and Anaphylactoid Reactions" U. Appl. Toxicol., 16, 1996: 25-33, Of Record.

Dryer, "$Na^+$-Activated $K^+$ Channels: a New Family of Large Conductance Ion Channels" Trends Neurosci., 17, 1994: 155-60, Of Record.

Faden, "Neorotoxic Versus Neuroprotective Actions of Endogenous Opioid Peptides: Implications for Treatment of CNS Injury" Nida. Res. Monogr., 163, 1996: 318-30, Of Record.

Fields et al., "Signalling Functions and Biochemical Properties of Pertussis Toxin-Resistant G-Proteins" Biochem. J., 321 (Pt3), Feb. 1, 1977:561-71, Of Record.

Fozzard et al., "The Guianidinium Toxin Binding Site on the Sodium Channel" Jpn. heart J., 37, 1996: 683-92, Of Record.

Harvey, "Presynaptic Effects of Toxins" Int. Rev. Neurobiol., 32, 1990: 201-39, Of Record.

Hille, "Modulation of Ion-Channel Function by G-Protein-Coupled Receptors" Trends Neurosci., 17, 1994: 923-42, Of Record.

Holstege et al., "Chemical Warfare. Nerve Agent Poisoning" Crit. Care Clin., 13, 1997: 923-42, Of Record.

Janiszewski, "The Action of Toxins on the Voltage-Gated Sodium Channel" Pol. J. Pharm, 42, 1990: 582-88, Of Record.

1994, Nisch et al., "A thin Film Microelectrode Array for Monitoring Extracellular Neuronal Activity in Vitro" Biosensors & Bioelectronics, GB, Elsevier Science Publishers, Barking, vol. 9, No. 9/10, pp. 737-741, Of Record.

Gross et al., "Stimulation of Monolayer Networks in Culture Through Thin-Film Indium-Tin Oxide Recording Electrodes" Journal of Neuroscience Methods, NL, Elsevier Science Publisher B.V., Amsterdam, vol. 50, 1993, pp. 131-143, Of Record.

Dec. 10, 1998, Pancrazio et al., "Portable Cell-Based Biosensor System for Toxin Detection" Sensors and Actuators B, CH, Elsevier Sequoia S.A., Lausanne, vol. 53, No. 3, pp. 179-185, Of Record.

1996, Mohr et al., "Performance of a Thin Film Microelectrode Array for Monitoring Electrogenic Cells in Vitro" Sensors and Actuators B 34, pp. 265-269, Of Record.

Kallen et al., "Structure, Function and Expression of Voltage-Dependent Sodium Channels" Mol. Neurobiol., 7, 1993: 383-428, Of Record.

Lewis et al., "Origin and Transfer of Toxins Involved in Ciguatera" Comp. Biochem. Physiol. C., 106, 1993: 615-28, Of Record.

Mori et al., "Molecular Pharmacology of Voltage-Dependent Calcium Channels" Jpn. J. Pharmacol., 72, 1996: 83-109, Of Record.

Narahashi et al., "Sodium and GABA-Activated Channels as the Targets of Pyrethroids and Cyclodiens" Toxicol. Lett., 1992: 429-436, Of Record.

Narahashi et al., "Recent Advances in the Study of Mechanism of Action of Marine Neurotoxins" Neurotoxicology, 15, 1994: 545-54, Of Record.

Nestler et al., "Molecular and Cellular Mechanism of Opiate Action: Studies in the Rat Locus Coeruleus" Brain Res. Bull., 35, 1994: 521-28, Of Record.

Norton, "Structure-Function Relationships of Sea Anemone Proteins that Interact with the Sodium Channel" Toxicon, 29, 1991: 1051-84, Of Record.

Pearson, "Modulation of Voltage-Dependent Calcium Channels in Cultured Neurons" Ann. N.Y. Acad. Sci., 747, 1994: 325-35, Of Record.

Pfister et al., "Interactions of a G-Protein with its Effector: Transducin and cGMP Phosphodiesterase in Retinal Rods" Cell Signal, 5, 1993: 235-41, Of Record.

Piek, "Neurotoxins from Venoms of the Hymenoptera—Twenty-Five Years of Rresearch in Amsterdam" Comp. Biochem. Physiol. C., 96, 1990: 223-33, Of Record.

Rizzo et al., "Mechanisms of Paresthesiae, Dysesthesiae, and Hyperesthesiae: Role of $Na^+$ Channel Heterogeneity" Eur. Neural., 36, 1996: 3-12, Of Record.

Rowan et al., Toxins Affecting $K^+$ Braz. J. Med. Biol. Res., 29, 1996: 1765-80, Of Record.

Savolainen et al., "Second Messengers in Cholinergic-Induced Convulsions and Neuronal Injury" Toxicol. Lett., Dec. 1992: 64-65 Spec No. 437-45, Of Record.

Schantz et al., "Properties and Use of Botulinum Toxin and Other Microbial Neurotoxins in Medicine" Microbial. Rev., 56, 1992: 80-99, Of Record.

Smith, "Strychnine Poisoning" [Published erratum appears in J. Emerg. Med., 9(6), Nov.-Dec. 1991: 555]; J. Emerg. Med., 8, 1990: 321-25, Of Record.

Solberg et al., "The Role of Excitotoxicity in Organophosphorous Nerve Agents Central Poisoning" Trends Pharmacol. Sci., 18, 1997: 183-85, Of Record.

Swift et al., "Ciguatera" IJ. Toxicol. Clin. Toxicol., 31, 1993: 1-29, Of Record.

Uchitel, "Toxins Affecting Calcium Channels in Neurons" Toxicon, 35, 1997: 1161-91, Of Record.

Van et al, "Pharmacological Effects of Oximes: How Relevant are they?" Arch. Toxicol., 70, 1996: 779-86, Of Record.

Wu, "Enhancement of Immunotoxin Activity Using Chemical and Biological Reagents" Br. J. Cancer, 75, 1997: 1347-55, Of Record.

Yoshida, "Tetradotoxin-Resistant Sodium Channels" Cell. Mol. Neurobiol., 14, 1994: 227-44, Of Record.

Riley, "Functions of Gene Products of *Escherichia coli*" Microbiol. Rev., 57, 1993: 862-952, Of Record.

Okuhara et al., Related Articles—"Corticosteriods Alter 5-Hydroxytryptamine 1A Receptor Effector Pathway in Hippocampal Subfield CA3 Pyramidal Cells" J. Pharmacol. Exp. Ther., 284(3), Mar. 1998: 1227-33, Of Record.

Miller et al., Related Articles—"Cholecystokinin Increases GABA Release by Inhibiting a Resulting $K^+$ Conductance in Hippocampal Interneurons" J. Neurosci., 17(13), Jul. 1, 1997: 4994-5003, Of Record.

Figenschou at al., Related Articles—"Cholinergic Modulation of the Action Potential in Rat Hippocampal Neurons" Eur. J. Neurosci., 8(1), Jan. 1996: 211-19, Of Record.

Brewer at al., Related Articles—"Optimized Survival of Hippocampal Neurons in B27-Supplemental Neurobasal, a New Serum-Free Medium Combination" J. Neurosci. Res., 35(5), Aug. 1, 1993: 567-76, Of Record.

1999, Wheeler, "Real Time Techniques for Automatic Discrimination of Single Units" Book chapter,in press, to "Methods for Neural Ensemble Recordings" M. Nicolelis (ed.), CRC Press. Of Record.

Hickman et al., "Molecular Self-Assembly of Two-Terminal Microsensors with Internal References" Science, 252, 1991: 688, Of Record.

Wheeler et al., "Multineuron Patterning and Recording" in McKenna & Stenger (Eds.) "Enabling Technologies for Cultured Neural Networks" Academic Press; 1994: 167-85, Of Record.

Ma et al., Neuronal and Glial Epitopes and Transmitter-Synthesizing Enzymes Appear in Parallel with Membrane Excitability During Neuroblastoma X Glioma Hybrid Differentiation, Developmental Brain Research 106 (1998) 155-163, Of Record.

Feb. 3, 2006, Mohan et al., "Toxin Detection Based on Action Potential Shape Analysis Using a Realistic Mathematical Model of Differentiated NG108-15 Cells" Biosensors and Bioelectronics 21 1804-1811, Of Record.

1991, Ulman, An Introduction to Ultrathin Organic Films from Langmuir-Blodgett to Self-Assembly, Academic Press, Inc., pp. 245-251, Of Record.

Dec. 1998, Sokal et al., "Differential Effect on Thapsigargin on Bicuculline- and Gabazine-Induced Epileptiform Excitability in Dissociated Rat Hippocampal Neurones," British Journal of Pharmacol., vol. 125 (Proceedings suppl.), abstract 40p, cited in view of the Guidelines, VI, 7.24.

Mohr et al., "Performance of a Thin Film Microelectrode Array for Monitoring Electrogenic Cells in Vitro" Sensors and Actuators, vol. 34, 1996, pp. 265-269.

Ambros-Ingerson et al., "Stimulation of Paleocortex Performs Hierarchical Clustering" Science, 247; 1990: 1344-48; Abstract.

Stenger et al., Related Articles—"Microlithographic Determination of Axonal/Dendritic Polarity in Cultured Hippocampal Neurons" J. Neurosci. Methods; Aug. 1; 82(2) 1998: 167-73; Abstract.

Narahashi et al., "Sodium and GABA-Activated Channels as the Targets of Pyrethroids and Cyclodiene" Toxicol. Lett., 1992: 429-436; Abstract.

Narahashi et al., "Recent Advances in the Study of Mechanism of Action of Marine Neurotoxins" Neurotoxicology, 15, 1994: 545-54.; Abstract.

Nestler et al., "Molecular and Cellular Mechanism of Opiate Action: Studies in the Rat Locus Coeruleus" Brain Res. Bull., 35, 1994: 521-28; Abstract.

Cowan et al., "Hypothesis for Synergistic Toxicity of Organophosphorus Poisoning-Induced Cholinergic Crises and Anaphylactoid Reactions" U. Appl. Toxicol., 16, 1996: 25-33; Abstract.

Pearson, "Modulation of Voltage-Dependent Calcium Channels in Cultured Neurons" Ann. N.Y. Acad. Sci., 747, 1994: 325-35; Abstract.

Pfister et al., "Interactions of a G-Protein with its Effector: Transducin and cGMP Phosphodiesterase in Retinal Rods" Cell Signal, 5, 1993: 235-41; Abstract.

LeMasson et al., "Activity-Dependent Regulation of Conductances in Model Neurons" Science, 259, 1993: 1915-17; Abstract.

Wu, "Enhancement of Immunotoxin Activity Using Chemical and Biological Reagents" Br. J. Cancer, 75, 1997: 1347-55; Abstract.

Apr. 21, 1995, Schaffner et al., "Investigation of the Factors Necessary for Growth of Hippocampal Neurons in a Defined System" Journal of Neuroscience Methods 62 111-119; Abstract.

Riley, "Functions of Gene Products of *Escherichia coli*" Microbiol. Rev.; 57; 1993: 862-952; Abstract.

Dryer, "Ne$^+$-Activated K$^+$ Channels: a New Family of Large Conductance Ion Channels" Trends Neurosci., 17, 1994: 155-60; Abstract.

Marder et al., "Theory in Motion" Curr. Opin. Neurobiol.; 5, 1995: 832-40; Abstract.

Schizas, "Learning Systems in Biosignal Analysis" Biosystems; 41, 1997: 105-25; Abstract.

Childres et al., "Role of Cyclic AMP in the Actions of the Cannabinoid Receptors" Biochem. Pharmacol., 52, 1996: 819-27; Abstract.

Catterall et al., "Molecular Properties of the Sodium Channel: a Receptor for Multiple Neurotoxins" Bull. Soc. Pathol. Exot., 85 (5 Pt 2); 1992: 481-85; Abstract.

Cassola et al., "Use of Neurotoxins to Study $Ca^{2+}$ Channel Functions" Braz. J. Med. Biol. Res., 29; 1996: 1759-63; Abstract.

Becerril et al., "Toxins and Genes Isolated from Scorpions of the genus Tityus" Toxicon, 35, 1997: 821-35; Abstract.

Brazil et al., "Toxins as Tools in the Study of Sodium Channel Distribution in the Muscle Fibre Membrane" Toxicon, 31; 1993: 1085-98; Abstract.

Faden, "Neorotoxic Versus Neuroprotective Actions of Endogenous Opioid Peptides: Implications for Treatment of CNS Injury" Nida. Res. Monogr., 163, 1996: 318-30; Abstract.

Fields et al., "Signalling Functions and Biochemical Properties of Pertussis Toxin-Resistant G-Proteins" Biochem. J., 321 (Pt3), Feb. 1, 1977:561-71; Abstract.

Fozzard et al., "The Guianidinium Toxin Binding Site on the Sodium Channel" Jpn. heart J., 37, 1996: 683-92; Abstract.

Harvey, "Presynaptic Effects of Toxins" Int. Rev. Neurobiol., 32, 1990: 201-39; Abstract.

Hille, "Modulation of Ion-Channel Function by G-Protein-Coupled Receptors" Trends Neurosci., 17, 1994: 923-42; Abstract.

Holstege et al., "Chemical Warfare. Nerve Agent Poisoning" Crit. Care Clin., 13, 1997: 923-42; Abstract.

Janiszewski, "The Action of Toxins on the Voltage-Gated Sodium Channel" Pol. J. Pharm, 42, 1990: 582-88; Abstract.

Kallen et al., "Structure, Function and Expression of Voltage-Dependent Sodium Channels" Mol. Neurobiol., 7, 1993: 383-428; Abstract.

Lewis et al., "Origin and Transfer of Toxins Involved in Ciguatera" Comp. Biochem. Physiol. C., 106, 1993: 615-28; Abstract.

Mori et al., "Molecular Pharmacology of Voltage-Dependent Calcium Channels" Jpn. J. Pharmacol., 72, 1996: 83-109; Abstract.

Piek, "Neurotoxins from Venoms of the Hymenoptera—Twenty-Five Years of Rresearch in Amsterdam" Comp. Biochem. Physiol. C., 96, 1990: 223-33; Abstract.

Rizzo et al., "Mechanisms of Paresthesiae, Dysesthesiae, and Hyperesthesiae: Role of Na$^+$ Channel Heterogeneity" Eur. Neurol., 36, 1996: 3-12; Abstract.

Savolainen et al., "Second Messengers in Cholinergic-Induced Convulsions and Neuronal Injury" Toxicol. Lett., Dec. 1992: 64-65 Spec No. 437-45; Abstract.

Okuhara et al., Related Articles—"Corticosteriods Alter 5-Hydroxytryptamine 1A Receptor Effector Pathway in Hippocampal Subfield CA3 Pyramidal Cells" J. Pharmacol. Exp. Ther., 284(3), Mar. 1998: 1227-33; Abstract.

Schantz et al., "Properties and Use of Botulinum Toxin and Other Microbial Neurotoxins in Medicine" Microbiol. Rev., 56, 1992: 80-99; Abstract.

Smith, "Strychnine Poisoning" [Published erratum appears in J. Emerg. Med., 9(6), Nov.-Dec. 1991: 555]; J. Emerg. Med., 8, 1990: 321-25; Abstract.

Solberg et al., "The Role of Excitotoxicity in Organophosphorous Nerve Agents Central Poisoning" Trends Pharmacol. Sci., 18, 1997: 183-85; Abstract.

Swift et al., "Ciguatera" IJ. Toxicol. Clin. Toxicol., 31, 1993: 1-29; Abstract.

Uchitel, "Toxins Affecting Calcium Channels in Neurons" Toxicon, 35, 1997: 1161-91; Abstract.

Van et al., "Pharmacological Effects of Oximes: How Relevant are they?" Arch. Toxicol., 70, 1996: 779-86; Abstract.

Cantiello, "Role of the Actin Cytoskeleton on Epithelial Na$^+$ Channel Regulation" Kidney Int.; 48, 1995: 970-984; Abstract.

\* cited by examiner

Single Action Potential

Spontaneous Beating

FIGURE 5

AP = Action Potential
FC = Functional Category

HIGH THROUGHPUT FUNCTIONAL GENOMICS

CROSS-REFERENCE TO RELATED APPLICATION

This application is a continuation of U.S. application Ser. No. 09/575,377, filed May 22, 2000, now U.S. Pat. No. 7,266,457, which is a non-provisional application that claims priority to U.S. provisional Application No. 60/135,275, filed May 21, 1999, the complete disclosure of which is incorporated herein by reference.

1. FIELD OF THE INVENTION

The present invention relates to an apparatus, processes, methods and systems for the analysis of samples and test substances, including drags, toxins, genes, gene products and the like. Moreover, the present invention discloses high throughput methods particularly suitable for conducting functional genomics studies by which information about the function of isolated nucleic acids can be obtained without resorting to cumbersome conventional methods like the creation of transgenic animals or animals in which one or more selected genes have been "knocked out." In particular, the present invention makes possible the gathering of the types of information about the physiological, pharmacological, or other biological effects of a sample or a test substance under conditions that mimic in vivo studies.

2. BACKGROUND OF THE INVENTION

At the present time, the only available "assays" based on cognitive or "cellular function" are living creatures. The use of *C. elegans* and *Drosophila* is predominant in these assays. In vitro cell cultures of embryonic rat and mouse tissue, especially through "knockout" technology, have also been used to study cellular organization and communication. However, in studies to date, single neurons have not been electrically integrated with modern electronics except in expensive patch-clamp methodology, which can be tedious, can result in disorganized cultures and are incapable of high throughput analysis. Imaging capabilities have been introduced using voltage-sensitive dyes. Such techniques are limited in their use, however, and dyes are generally toxic to neurons, as already mentioned above.

Therefore, it is clear that there is a lack of in vitro assays for studying neurotoxicity, for example, which are based on a cell's function. There are also very few methods of measuring toxicity other than morphological analysis. There is also a problem performing chronic electrophysiological monitoring of cells by standard electrophysiology. What is more the field of genomics lacks a high throughput assay to analyze the large number of sequences and genes being uncovered by the human genome project. Thousands upon thousands of new compounds are also being generated by recently utilized combinatorial chemical synthesis methods.

The use of biological cells and their underlying cellular functions as model systems for information processing is being investigated for a number of practical applications. Algorithms that are based on olfactory processing (Ambrose-Ingerson, J., Granger, R., and Lynch, G. (1990). *Science* 247: 1344-1348.; Granger, R., Ambrose-Ingerson, J., Anton, P. S., Whitson, J. and Lynch, G. (1991). *An Introduction to Neural and Electronic Networks*, eds. Zornetzer, S. F., Davis, J. L., and Lau, C. (Academic Press, Inc., San Diego), pp. 25-42.), computing using DNA in a test tube (Adleman, L. (1994). Molecular Computation of Solutions to Combinatorial Problems. *Science* Vol. 266.), or possibly manipulation of DNA in bacteria or other cells are just some examples. Recent articles have focused on bioinformation and the creation of biological pathways or genetic circuits using silicon-based models (Palsson, 1997). Experiments on tissue slice preparations, in cultured neuronal networks (Gross. G. W., Rhoades, B. K., Azzazy, H. M. E., & Wu, M. C., (1995). The use of neuronal networks on multielectrode arrays as biosensors. *Biosens. Bioelectron.*, 10, 553-567.; 1: Stenger D A, Hickman J J, Bateman K E, Ravenscroft M S, Ma W, Pancrazio J J, Shaffer K, Schaffner A E, Cribbs D H, Cotman C W. Related Articles Microlithographic determination of axonal/dendritic polarity in cultured hippocampal neurons J Neurosci Methods. 1998 Aug. 1; 82(2): 167-73.) and with single neurons (e.g. LeMasson, G., E. Marder and L. F. Abbott (1993) Activity-dependent regulation of conductances in model neurons. *Science* 259, 1915-7.; Marder, E. and L. F. Abbott (1995) Theory in motion. Curr Opin Neurobiol 5, 832-40.; Schizas, C. N. and C. S. Pattichis (1997) Learning systems in biosignal analysis. Biosystems 41, 105-25.) are being studied using dual patch-clamp electrophysiology and imaging systems. Many others have proposed "in silica" models of intracellular function as precursors to programming cells for biological computation. See, e.g., U.S. Pat. No. 5,648,926 to Douglas et al., the contents of which are incorporated herein by reference. This application describes a hybrid system to elucidate cellular information in an efficient manner. There is a need to combine new algorithms to reproduce physiological conditions found in human, or modeled using data obtained with *C. elegans* and *Drosophila* that combines speed and utility of silicon systems and the relevance of cellular physiology to create new biological/non-biological high throughput assays.

With the increased capacity to uncover, isolate, discover, or create new substances (or even finding new uses for old substances), including new genetic materials, the need for a "functional assay," which provides some idea of the potential effects, roles, or functions of the test substance, is even more acute. One can look at function from the standpoint of what is the function or role of molecules, compounds and proteins in an organism. One can also look at function from the standpoint of how collections of molecules, compounds and proteins create or affect pathways that are combined to comprise functional categories in a cell such as energy metabolism, extracellular signaling, transcription, or protein synthesis. These pathways underlie the processes and functions that maintain a cell and their identification helps to establish the identity and role or "cellular function" of the lest substance in a higher organism. Particular groups of cells having unique "cellular functions" are intermixed in an organized fashion to create a higher organism such as an animal.

Traditionally, it has been difficult to assay the effect of a compound or protein on a cell's internal "functional categories" without observing the whole organism over a period of lime. Many assays have been developed to gain information before resorting to experiments at the whole organism level, with mixed results. In vitro biochemical assays attempt to reproduced some of these pathways outside the cell, but such assays lack the interactions with the myriad of other pathways in the cell.

Fluorescence probes, microsensors and electrophysiological recordings have supplied a wealth of information but suffer from many drawbacks. Patch-clamp electrophysiological recordings can provide acute measurements but the experimental conditions lead to cell death. This drawback also applies to most fluorescent probes, which can cause toxic effects through photobleaching. Thus, a need exists in drug discovery, functional genomics and basic science for an assay that provides information and data about molecules, compounds and proteins (or their genes) as these substances interact non-invasively with a living cell and its various cellular pathways or functional categories over a period of time. Preferably, information and data about the various cellular pathways or functional categories, which are affected, are obtained from such an assay. More preferably, it would be desirable if such information and data could be captured electrophysiologically. If one can combine such features with simple sample preparation and if such an assay allows many conditions to be tested quickly on a statistically relevant number of cells, then one will have provided a very useful assay having a high throughput cellular functional capacity and which can provide much of the information that formerly could only be obtained through experiments at the whole organism level or by extensive and time consuming experimentation. A wide variety of biological compounds affect cellular functions. Marder has shown that greater than 40 biochemicals are involved in just the communication between neurons in the lobster digestive system. (Marder, E. and L. F. Abbott (1995) Theory in motion. Curr Opin Neurobiol 5, 832-40.) Many of these biochemicals are specific for ion channels, but many more act through receptors. Similar information for other systems about the interaction of known biochemicals and cellular processes or pathways can also be gleened from any neuroscience text. In addition, there is a wealth of clinical and epidemiological data that shows how a whole host of compounds affect cellular function, for example.

By indirect reference, the applicant believes that a large number of these biochemicals must affect the membrane potential of an affected cell in some way. For example, some compounds (such as saxitoxin) operate by inhibition of the sodium ion channel. Others, such as tetraethylammonium chloride (TEA) operate by acting on the potassium channel. Still other compounds activate intracellular cascades leading to calcium mobilization and specific gene activation. Hence, the applicant describes herein, systems, devices and methods that exploit the effects of biochemicals on inter alia the membrane potential. Accordingly, the applicant has discovered that one can characterize the changes in an action potential obtained from an electrically active cell following the addition of specific biochemical compounds or "triggers" to such electrically active cells (e.g., neuronal cells) using planer microelectrodes that enables elucidation of the cellular function relevant to drug discovery or functional genomics. It should be noted that a particular embodiment of the changes in a membrane potential are the changes that can be observed in an action potential. Hence, an electrically active cell is one that exhibits perceptible (measurable) changes in its membrane potential, more preferably, one that exhibits perceptible changes in its action potential.

Examples of biochemicals of interest include, but are not limited to, those that elicit changes in signals via the following mechanisms: (a) phosphatidylinositol turn-over; (b) calcium mobilization; (c) phosphorylation of intracellular protein messengers; (d) ion channel blockers ($Na^+$, $K^+$, $Ca^{2+}$, etc.); and (e) cAMP formation. Biochemicals can also be selected for their inhibitory properties on specific pathways, such as neurotransmission inhibitors and protein synthesis inhibitors. Some of these compounds have been shown to affect the membrane potential and other individual ion channels.

Surface modification technology utilizing Self Assembled Monolayers (SAMs) is a known process for preparing a modifying layer composed of organic molecules, which can spontaneously form strong interactions or covalent bonds with reactive groups on an exposed surface. The utilization of SAMs for modifying surfaces has been demonstrated on electronic materials such as silicon dioxide, biodegradable polymers and oilier polymers such as Teflon. A large variety of functional groups or combination of functional groups can be located on the terminus opposite the attachment point of a SAM, and the chemical composition can be manipulated to systematically vary the surface free energy. Biological cells can attach to, and proliferate on SAMs, and SAMs can be used to pattern a surface. SAMs are also useful to set as templates for the patterning of biomolecules, especially antibodies. SAMs thus can prove to be an ideal tool for the design of artificial surfaces for the tailoring of cellular interactions.

Metal microelectrodes surrounded by an insulator can be used to record the electrical activity of cells extracellularly. The applicant has surmised that if the interface can be tailored to keep the cells on the microelectrodes, a viable system can be created for high throughput cell assays. The applicant believes that this type of system can be fabricated by taking advantage of previous work involving orthogonal self-assembly on two different metals (sec, e.g., Hickman, J. J. Laibinis, P. E., Auerbach, D. I., Zou, C, Gardner, T. J., Whitesides, G. M., and Wrighton, M. S. (1992). Toward orthogonal self-assembly of redox active molecules on Pt and Au: Selective reaction of disulfide with Au and isonitrile with Pt. *Langmuir* 8: 357.) and on a surface composed of a metal and an insulator coating region. See, also, U.S. Pat. No. 5,223,117 to Wrighton et al., the contents of which are incorporated herein by reference.

Surface analysis techniques have been applied to analyze cell culture surfaces both before and after culture and to relate the quantitative and qualitative results to cell morphology and survival. (See, e.g., Schaffner, A., Barker, J. L., Stenger, D. A., and Hickman. J. (1995). Investigation of the factors necessary for growth of hippocampal neurons in a defined system. *J. Neurosci. Methods,* 62, 111-119.) Previous studies by others have also correlated cell behavior to the initially quantified properties of the culture surface, i.e., prior to the addition of cells. Many components of the culture medium adsorb onto the surface, and cells secrete substances that comprise an extracellular matrix (ECM), as well as soluble molecules. Many of these biomolecules potentially are the source of the cell behavior monitored and can be a valuable source of information.

One problem encountered using a cell line as the sensor element is that cell lines (e.g., NG108-15, which is derived from a gliomaxneuroblastoma) have an inherently unstable genome. The applicant considers primary cells to be very relevant to the present system because it is presumed that such cells more closely approximate in vivo systems than tumor-derived cell lines; however, primary cells tend to be difficult to culture and are in homogeneous. A possible solution to these drawbacks involves the utilization of clonal cell lines derived from CNS stem cells. Thus, a preferred cell having a stable long-lived phenotype is one derived from a stem cell. In the present invention, each individual cell becomes a unique assay element with the cells localized on individual microelectrodes. Statistics can be performed on a reproducible population in response to a compound that is introduced into the media. Further we will apply system level algorithms to enable the reproduction or representation of relevant physiological states or reproductions of known assays employed by pharmaceutical or other biotechnology companies.

Hence, the present invention hopes to provide an assay of cellular function, using "functional categories" within the cell as defined, for example, by Riley, M. (1993). Functions of gene products of *Escherichia coli. Microbiol. Rev.* 57, 862-952. The present system is validated by taking known biochemicals with known functions and monitoring the changes in electrical potential upon introduction of the known biochemicals in the media. The present invention and its broadly applicable techniques would add a new paradigm in molecular function analysis, including gene function analysis. It is also possible to map cells in varying stages of development, as the present techniques can be applied using embryonic cells. Particularly useful cells include CNS cells, but the present approach can be used on any cell type that permits the monitoring of electrical changes in the membrane potential. It is hoped that a clear need for the present invention has been established by the discussion presented herein.

3. SUMMARY OF THE INVENTION

Accordingly, the present invention is directed to systems, devices, processes and methods for determining the effects of test substances, including their physiological or pharmacological effects on cells. Convenient measures of the effects of test substances are the effects on the electrical activity of cells, which electrical activity can be manifested by cells in a number of ways, including changes in membrane potential. In particular, one can measure changes in a cell's action potential, which can be considered an expression of the chances in membrane potential over a given lime period. Thus, the present applicant has discovered that the effects of test substances can be studied and revealed by recording and examining the changes in the electrical characteristics of electrically active cells, which changes are a reflection of the effects of the test substance on the physiology of the cell, including effects on underlying cellular processes, mechanisms, or pathways. The present invention, then, can serve as an important measure of the biological activity of a test substance or, at least, an indicator of potential biological activity of a test substance in certain categories of cellular function. Such measurements or indications are conveniently made available without resorting to the use of in vivo models and represent a significant advance in the art.

In particular, the present invention seeks to provide systems and methods for the deconvolution of an action potential recorded from an electrically active cell, which cell is positioned on the surface of a solid state microelectrode. More particularly, a cell is exposed to a variety of conditions, and the effects of those conditions, or changes in such conditions, on the observed action potential are noted. Making use of the knowledge accumulated about the physiological, pharmacological and related effects (e.g., mechanistic pathways elucidated in the literature) of known substances, the present invention makes possible the further elucidation of the changes in one or more characteristics of the electrical activity of a cell (as reflected, for example, in its action potential), which changes can thus be associated or correlated with the specific effect or mechanistic pathway identified with each substance or combinations thereof. Hence, in a specific embodiment of the present invention, a body of knowledge is provided which permits the examination of test substances to determine their effects on the action potential and, in turn, on the underlying processes or functional categories of the cell affected by the test substances.

In a specific embodiment of the invention, a system is provided, which is capable of identifying one or more ion channels of a cell, which channels are affected by a test substance. Such a system comprises a device, which is optionally accompanied by software (e.g., a computer program, data processing application, algorithm and the like), in which the device comprises: (a) a solid state microelectrode; (b) a cell culture comprising one or more electrically active cells having a cell membrane including one or more ion channels, which one or more cells are capable of providing a measurable change in their electrical characteristics (for example, provides a measurable action potential that exhibits one or more perceptible characteristics); (c) an intervening layer which (i) comprises a surface modifying agent, and (ii) is positioned between the microelectrode and the one or more cells of the cell culture, such that a high impedance seal is provided at least in the vicinity of the one or more cells of the cell culture. The optional accompanying software comprises instructions that can be implemented by a computer and which are capable of relating changes in the one or more characteristics exhibited by the electrical activity (e.g., exhibited by the action potential) to one or more ion channels of the one or more cells upon exposure of the one or more cells to a lest substance. More particularly, the applicant conceives of a high impedance seal that reduces the lateral flow of ions across the microelectrode from the surrounding medium, while permitting or facilitating the vertical flow of ions between the cell and the microelectrode. In this manner, the microelectrode is best suited to detect changes in the ion flux attributable to the cell and not due to the surrounding medium.

The present invention contemplates a system in which the one or more characteristics exhibited by the membrane potential or action potential is manifested in its waveform or a derivative thereof. In still other embodiments, the one or more characteristics include at least one of after potential, time to cessation of activity, frequency, amplitude, shape, spike rate, or time constant. In preferred embodiments of the present invention, the data processing instructions are further capable of receiving input data comprising data on the temporal description of the membrane potential, action potential, or the changes therein.

In still additional embodiments, a system is provided in which data processing instructions are further capable of receiving input data comprising data on ion flux through ion channels selected from the group consisting of sodium channels, potassium channels, calcium channels, or combinations thereof. Other aspects of a system of the invention include utilization of a planar microelectrode in which the microelectrode can be a field effect transducer (FET). It is further contemplated that the system further comprises an insulator that surrounds the metal microelectrode or covers the gate of the FET. A suitable insulator includes materials selected from, but not limited to, the group consisting of silicon, modified silicon dioxide, silicon nitride, silicon carbide, germanium, silica, gallium, arsenide, epoxy resin, polystyrene, polysulfone, alumina, silicone, fluoropolymer, polyester, acrylic copolymers, polylactate, or combinations thereof.

A suitable cell culture for use in the present invention comprises an electrically active cell, which can include any metabolically active cell. Examples include, but are not limited to a neuronal cell or a cardiac cell. Preferably, the system makes use of a NG-108 cell. Still other cell cultures comprise a hippocampal cell, a stem cell, a transformed stem cell, their respective progeny, or combinations thereof. Moreover, one can contemplate the use of a stem cell or other progenitor or precursor cell, which has been exposed to a differentiating factor.

The present invention includes the use of a surface modifying agent, preferably comprising a self-assembling monolayer. Examples of suitable surface modifying agents include, but are not limited to, silanes, thiols, isocyanides, polyelectrolytes and the like, or combinations thereof. More preferably, the system incorporates an intervening layer that further comprises cell anchorage molecules. Suitable cell anchorage molecules include, but are not limited to, antibodies, antigens, receptor ligands, receptors, lectins, carbohydrates, enzymes, enzyme inhibitors, biotin, avidin, streptavidin, cadherins. RGD-type peptides, integrins, cadherins, modified lipids, or combinations thereof.

In a specific embodiment of the present invention the intervening layer comprises a high viscosity mixture comprising alcohols, ethers, esters, ketones, amides, glycols, amino acids, saccharides, carboxymethylsaccharides, carboxyethylsaccharides, aminosaccharides, acetylaminosaccharides, polymers thereof, or combinations thereof. In a preferred embodiment of the invention, the cell culture is coated with a polymer, such as cellulose, methylcellulose, dextran and the like. Still other features of a preferred embodiment of the invention include an intervening layer that can be characterized as either an attractive layer or a repulsive layer. The preferred system further comprises a detector circuit. One might also use cells transfected with endogenous or exogenous nucleic acid as the one or more cells of the cell culture. In such a case, the nucleic acid can comprise a nucleotide sequence associated with known or unknown function.

It is also an object of the invention to provide a method of determining one or more ion channels that are affected by a test substance comprising: (a) contacting a substance to be tested with a device comprising a solid state microelectrode; a cell culture including one or more cells having a cell membrane including one or more ion channels, which one or more cells are capable of providing a measurable action potential that exhibits one or more perceptible characteristics; and an intervening layer that is acting as a high impedance seal and which is positioned between the microelectrode and the cell culture; (b) collecting data on the action potential, the one or more characteristics thereof, or one or more changes therein; and (c) determining from the data the one or more ion channels that are affected by the test substance. In specific embodiments of the present invention, the test substance comprises a toxin, a drug, a pathogen, a neurotransmitter, a nerve agent, or mixtures thereof. Preferably, the method utilizes a determining step that includes deconvoluting the action potential, the one or more characteristics thereof, or the one or more changes therein.

The present invention is also directed to a system by which one can use algorithms that mimic physiological states or conditions of interest to gauge or determine the benefits, effects, side effects, or unintended consequences, etc. of test substances under such test conditions. For example, the system contemplated by the present invention can be manipulated so that particular pathways are turned on or off or are isolated in a way that provides the best scenario for observing the resulting behavior of a cell (e.g., a neuronal cell) upon exposure to one or more given test substances. As another example, one might be interested to know what the effects of a candidate drug for depression might have on individuals having high blood sugar levels e.g., diabetics or simply people who have just consumed a high carbohydrate meal or who are on a certain diet), or low blood sugar levels (e.g., hypoglycemics), or on individuals with high cholesterol. The system of the present invention can then be adjusted (where the adjustment of the variables of the system are controlled and kept track of by a system computer program or other accompanying system software), for example, by the addition or removal of cell culture nutrients, the transfection of the cells of the cell culture with a given nucleic acid or exposing them to a protein, peptide, or small molecule, changing the chemical or electrochemical characteristics of the media to the cell culture and the like. In this manner, the system of the present invention is able to provide information on physiological or pharmacological effects of drug candidates, which were previously available only from animal or human studies.

Accordingly, in another aspect of the present invention, a system is contemplated having a high throughput capacity to determine potential physiological effects of a test substance comprising a device and accompanying software, in which the device comprises a solid state microelectrode and a cell culture comprising one or more cells that exhibit electrical activity or, preferably, which are capable of providing a measurable action potential that exhibits one or more perceptible characteristics. The system can also optionally comprise accompanying software, which itself comprises data processing instructions capable of relating changes in the electrical activity or, preferably, in the one or more characteristics exhibited by the action potential to one or more potential physiological effects exerted by a test substance upon exposure of the test substance to the one or more cells of the cell culture. In particular, such a device may further comprise an intervening layer that is acting as a high impedance seal and which is positioned between the microelectrode and the one or more cells of the cell culture, and in which the accompanying software further comprises instructions, which can be implemented by a computer, for manipulating one or more system parameters to alter one or more conditions of a given experiment, for interpreting the outcome of such manipulations, or for both. Of course, separate software programs can be written to divide specific tasks, as dictated by system requirements, design, or convenience.

The present invention contemplates manipulations that include the addition of a compound of interest to the cell culture or the removal thereof from the cell culture. In particular, the compound of interest might be a nutritive material or a cell modulator, and the data processing instructions may include a temporal analysis of the action potential or the changes observed therein. More specifically, the data processing instructions is capable of providing an output suggestive of the involvement of one or more cellular pathways or receptors of interest. The present system preferably may be accompanied by software that includes instructions for a feedback loop to provide for flexibility in the manipulation of the parameters of the system to enhance or maximize the desired outcomes.

An object of the present invention is the realization of a system that is capable of determining a mode of action of a test substance based on the one or more cellular pathways or receptors of interest involved.

In a system of the present invention, the test substance might comprise a toxin, a drug candidate, a pathogenic agent, a neurotransmitter, a nerve agent, a gene, a gene product, or mixtures thereof. Consistent with the objectives of the present invention, a system is provided for determining one or more potential functions of an isolated nucleic acid, its expression product, or one or more active fragments of the nucleic acid or expression product, comprising a device and accompanying software, in which the device comprises a solid state microelectrode and a cell culture comprising one or more cells that are capable of providing a measurable action potential that exhibits one or more perceptible characteristics and which cells have been either transfected with an isolated nucleic acid or exposed to its expression product, and in which the accompanying software comprises data processing instructions capable of relating changes in the one or more characteristics exhibited by the action potential to one or more potential functions of the isolated nucleic acid, its expression product, or one or more active fragments of the nucleic acid or expression product.

Yet another object of the present invention involves a method of determining one or more potential functions of an isolated nucleic acid, its expression product, or one or more active fragments of the nucleic acid or expression product comprising (a) providing a device comprising a solid state microelectrode; a cell culture comprising one or more cells that are capable of providing a measurable action potential that exhibits one or more perceptible characteristics and which cells have been either transfected with an isolated nucleic acid or exposed to its expression product, (b) collecting data on the action potential, the one or more characteristics thereof, or one or more changes therein; and (c) determining from the data the one or more potential functions of the isolated nucleic acid, its expression product, or one or more active fragments of the nucleic acid or expression product. As in other embodiments of the present invention, a preferred determining step is one that includes deconvoluting the action potential, the one or more characteristics thereof, or the one or more changes therein; one that further comprises manipulating one or more parameters to alter one or more conditions of a given experiment; and one that further comprises interpreting the outcome of such manipulations.

Still another aspect of the present invention involves a computer readable medium encoding a program that includes instructions for execution by a computer, which instructions comprise data processing steps that relate changes in one or more characteristics exhibited by an observed action potential to one or more ion channels of one or more cells of a cell culture upon exposure of the one or more cells to a test substance. Specifically, the computer readable medium of the present invention is one in which the data processing steps may comprise a deconvolution step by which the changes in the one or more characteristics exhibited by the observed action potential are compared with stored information from past observations allowing the computer to attribute the changes to the one or more ion channels of the one or more cells. It is important to note that in preferred embodiments of the present invention, the computer readable medium relating to deconvolution of an action potential (or the deconvolution software) is one in which the data processing steps do not include a spectral analysis, more particularly, not including a spectral analysis that makes use of a Fourier transform. In particular, the deconvolution step of the present invention is inspired by biological knowledge. That is, our knowledge of the effects or mechanisms by which certain known substances act on the physiology of a cell is utilized by the methods of the present invention to more effectively analyze or deconvolute an action potential to more effectively relate changes in an action potential to underlying processes or pathways. It has thus been discovered that certain functional categories can be elucidated by the present deconvolution step. Hence, at a minimum, one can expose the system of the present invention to a test substance and through the deconvolution process be able to "fit" the effects of test substance on the action potential recorded by the system to one or more of these functional categories. The determination of the functional categories, in which a test substance best fits, is thus an object of the present invention.

Separately, another computer readable medium is provided which permits the parameters of the system to be changed and/or manipulated such that experimental conditions can be varied. In particular, the instructions encoded into a preferred computer readable medium are capable of customizing the system to provide desired outcomes on exposure of the system to one or more test substances. Such a "system software" may make of other programs, including deconvolution software. It is important to note that while the present invention's deconvolution software preferably excludes spectral analysis, more specifically, a Fourier transformation, the present invention's system software may utilize such spectral analysis or Fourier transformation.

Yet another object of the present invention is to disclose a system comprising: a solid state microelectrode; a cell culture which exhibits a measurable action potential; an intervening layer comprising a surface modifying monolayer, which functions as a high impedance seal; and software capable of analyzing the action potential to elucidate a cellular pathway or a receptor of interest. It is a further embodiment of the present invention, a system is disclosed in which the solid state microelectrode is a planar microelectrode.

A method is also disclosed, which relates to a high throughput analysis, the method comprising: providing a solid state microelectrode with an intervening layer comprising a surface modifying agent, preferably a self-assembling monolayer, which functions as a high impedance seal; adding a cell culture which exhibits a measurable action potential; and analyzing the action potential of the cell culture. In a further embodiment of the invention, additives are optionally introduced into the system.

The present invention also contemplates an apparatus comprising: a system that includes the following elements: a microelectrode; a cell culture which exhibits a measurable action potential; an intervening layer comprising a surface modifying agent, which functions as a high impedance seal; and software capable of analyzing the action potential to elucidate a cellular pathway or a receptor of interest; and a system algorithm capable of manipulating the elements of the system to develop an assay of interest. An embodiment of the invention is an apparatus that functions as an assay for determining the mode of action of a drug candidate on one or more cellular pathways or receptors.

In a specific embodiment of the present invention, a system is provided in which the one or more cells of the cell culture comprise cells transfected with at least one gene (e.g., one of unknown gene function), and in which the system algorithm is capable of manipulating the elements of the system to assist in the elucidation of effects of the gene on the behavior of the system or for the discovery of gene function.

Still a further object of the present invention is to provide a method of detecting an agent comprising: providing an agent; permitting the agent to interact with a sensor, in which the sensor comprises a cell culture having at least one cell which exhibits a measurable membrane potential, a solid state microelectrode, and an intervening layer that functions its a high impedance seal; observing or recording a change in the membrane potential; and analyzing the change in the membrane potential to elucidate a cellular pathway, ion channel, receptor of interest, or the like, which is affected by the action of the agent.

Other objects of the present invention will be apparent to (hose of ordinary skill in the art in view of the discussion and descriptions provided herein.

4. BRIEF DESCRIPTION OF THE FIGURES

Figure 4:
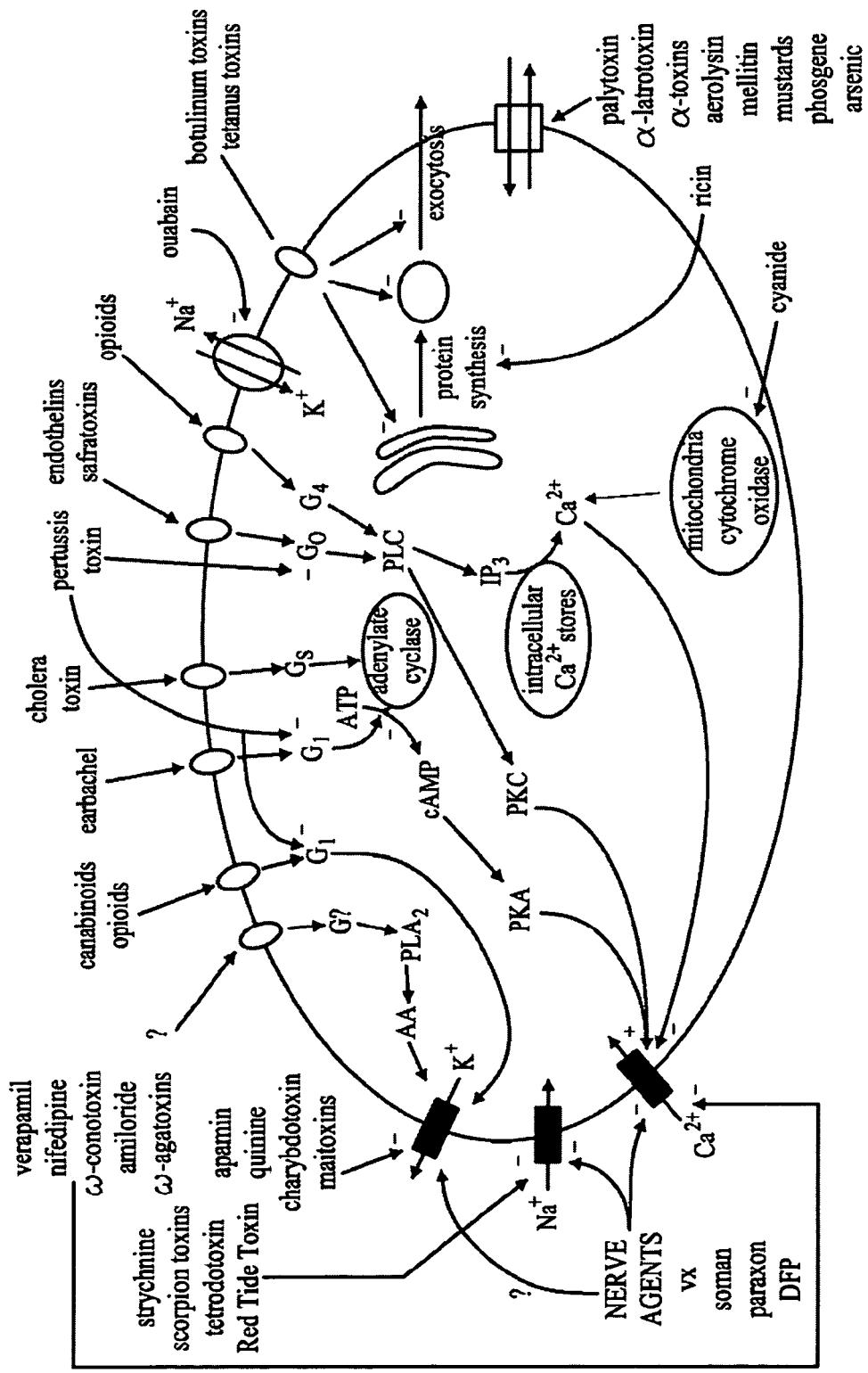

FIG. 4 illustrates a schematic model of some relevant receptors and intracellular pathways for a NG108-15 cell. Bold face indicates toxins that have been tested. The effect of toxins on action potential occurs within 60-180 seconds, except for VX, which occurs in 15 minutes.

Figure 5:
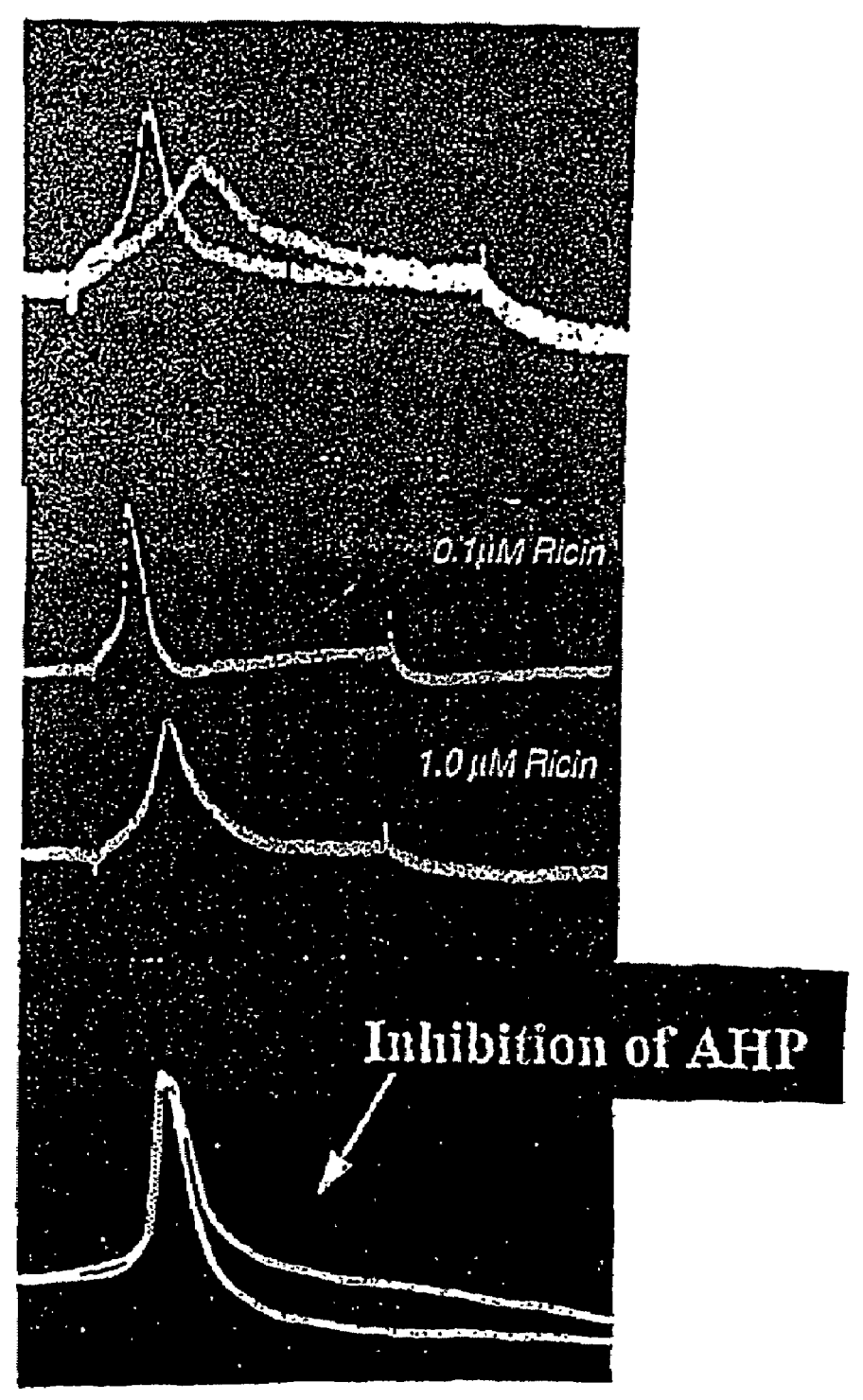

FIG. 5 illustrates results of administration of paraoxon (a nerve agent stimulant with an $LD_{50}$ of 1.8 mg/kg), ricin and cyanide on NG-108-15 cells. The stimulated action potential using intercellular recording shows the dramatic changes in action potential shape for the duration, amplitude and after hyperpolarization potential (AHP).

Figure 6A:
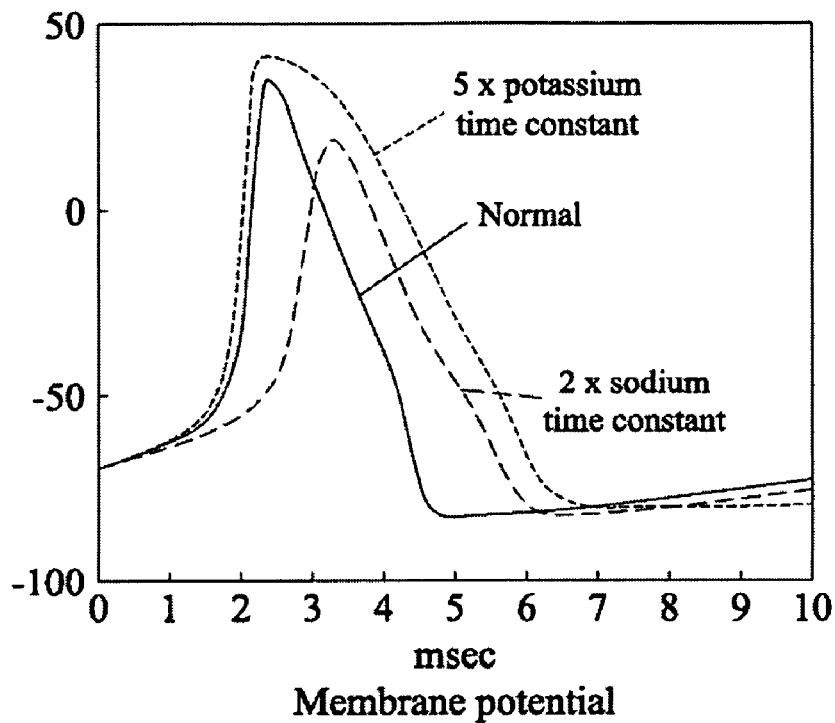
Figure 6B:
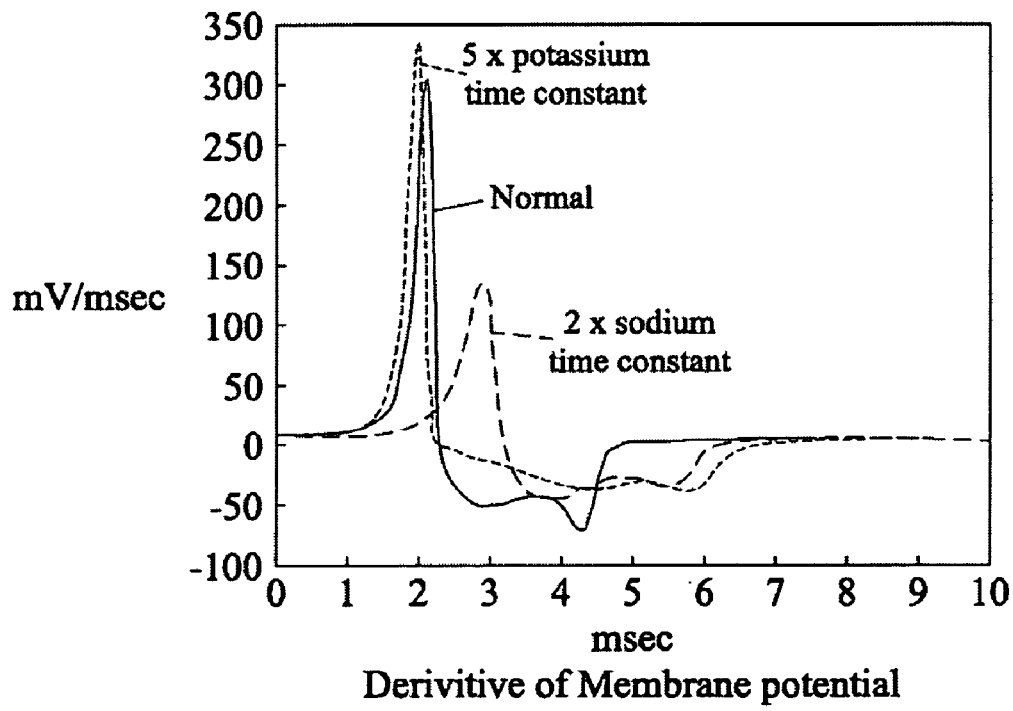

FIG. 6 show Hodgkin-Huxley simulations (a—membrane potential; b—derivative of membrane potential) to illustrate sensitivity of extracellular waveforms to changes in membrane lime constants. The largest peak is from a simulation in which the potassium channel time constant was lengthened by a factor of five—note the longer after potential. The smallest of the peaks results from increasing the sodium time constant by a factor of two. The remaining peak is the normal "textbook" Hodgkin-Huxley simulation.

Figure 7:
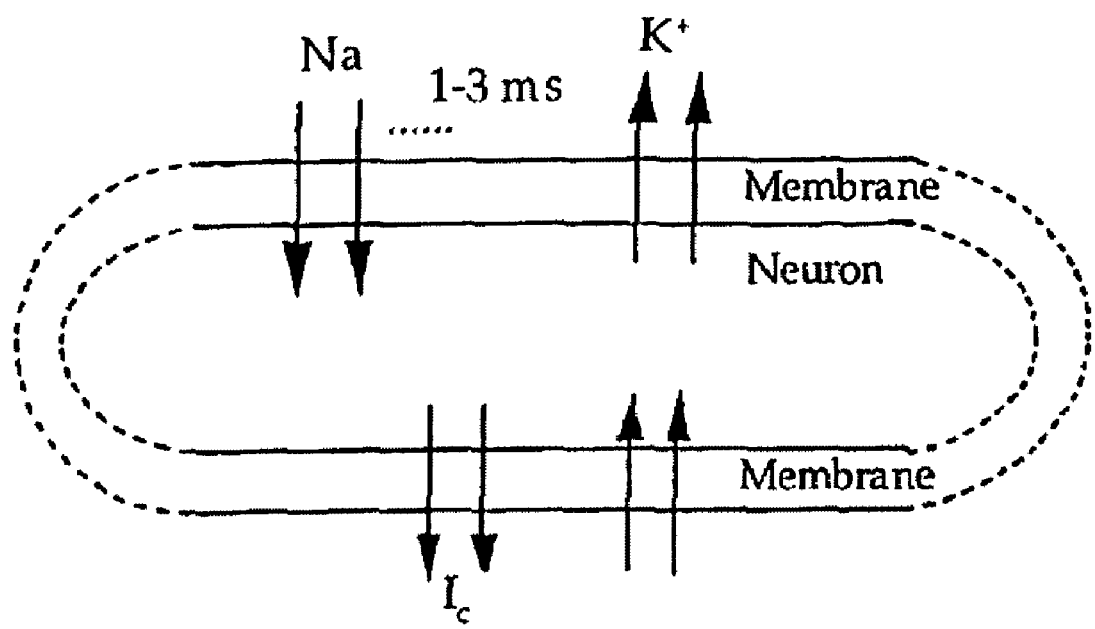

FIG. 7 illustrates a schematic of the neuron-to-microelectrode interface, where the capacitive discharge current= $(1_c)=C^{dv/dt}$.

Figure 8:
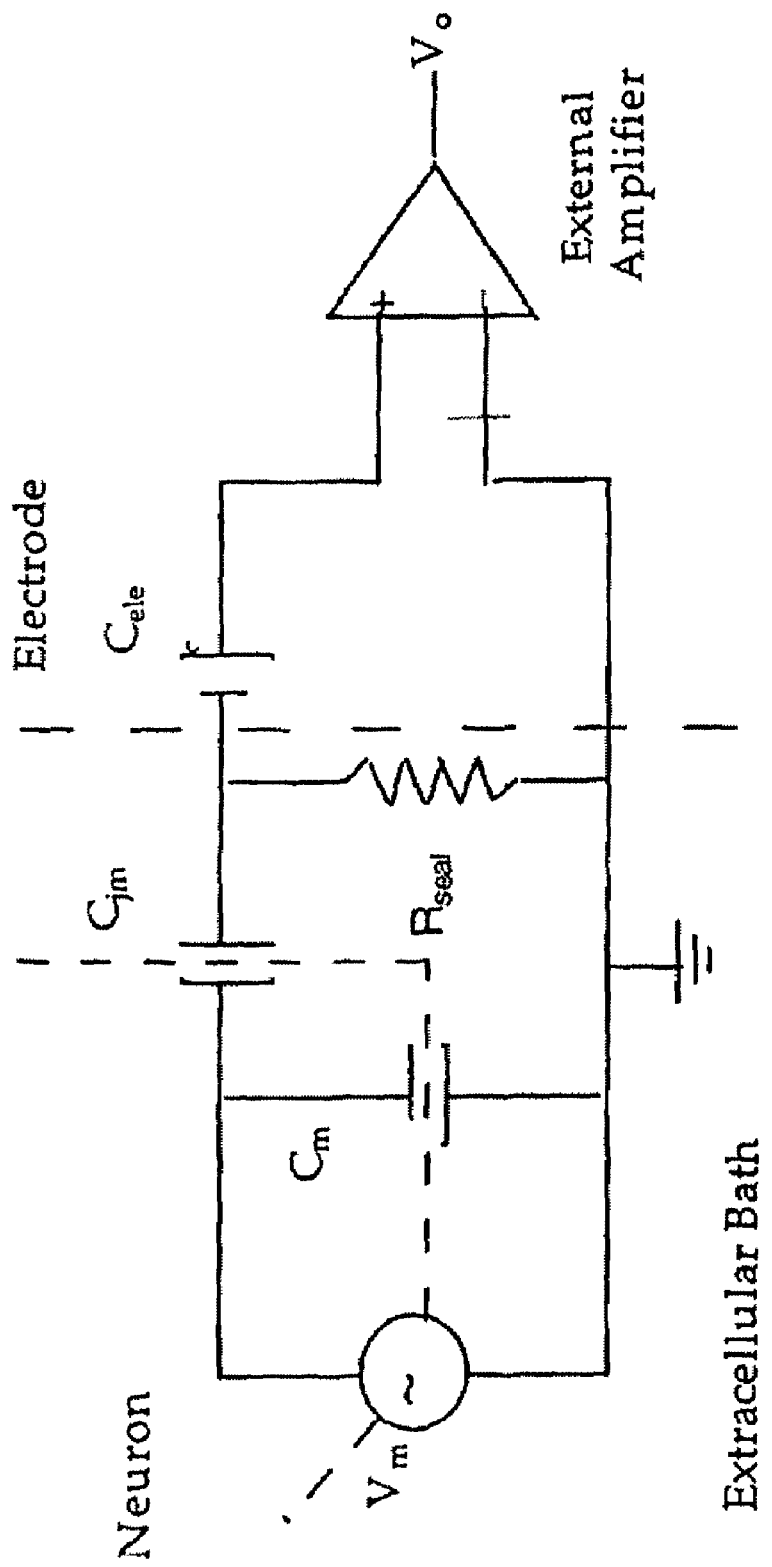

FIG. 8 illustrates an equivalent circuit for the neuron-microelectrode interface, adapted from Fromherz et al., (Fromherz, P., Offenhausser, A., Vetter, T., & Weis, J. (1991). A neuron-silicon junction: A Retzius cell of the leech on an insulated-gate filed-effect transistor. *Science* 252, 1290-1293.)

Figure 9:
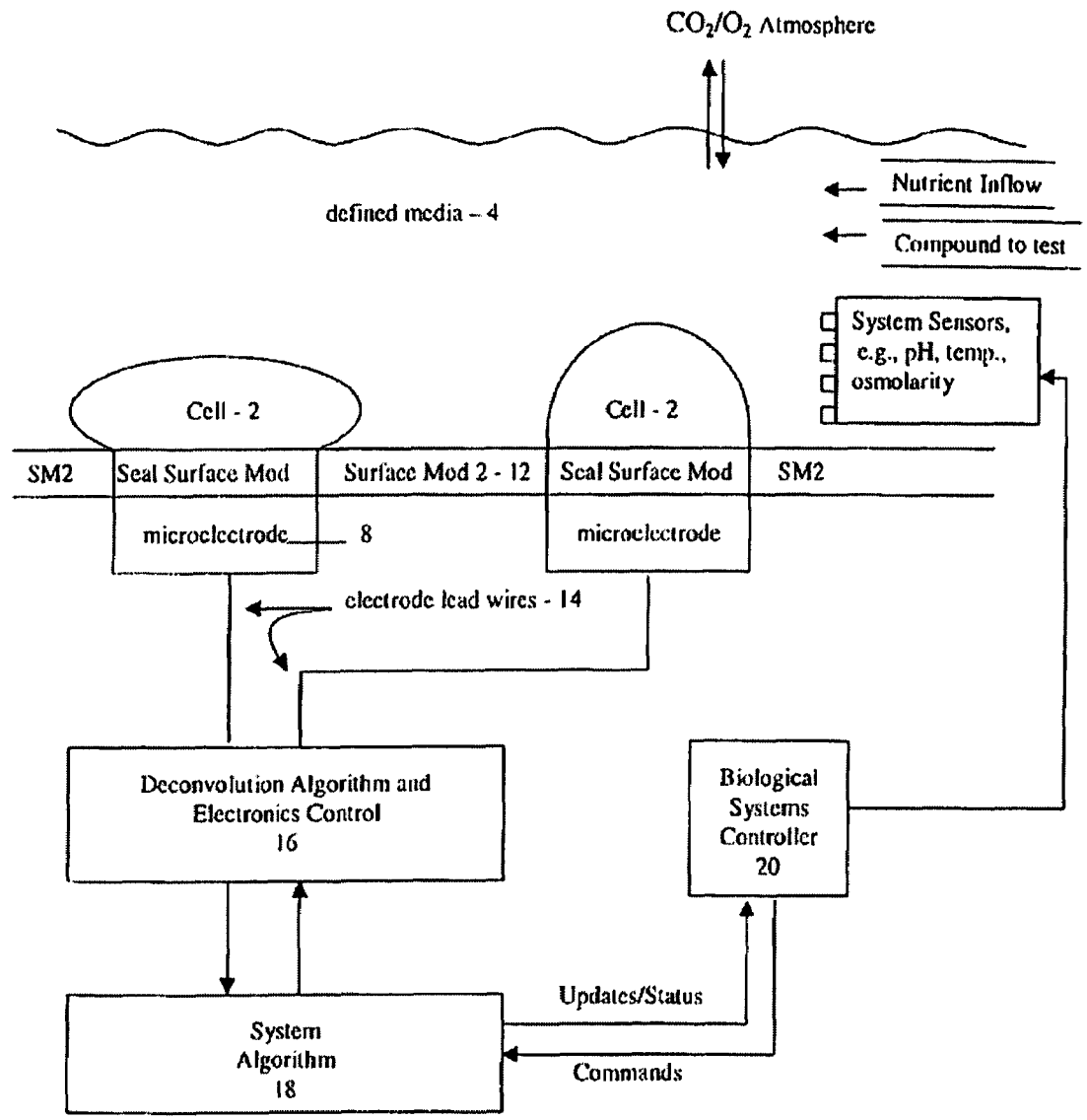

FIG. 9 illustrates a stacked view of the apparatus, as well as preferred connectivity diagram for a specific embodiment of a system of the present invention.

Figure 10:
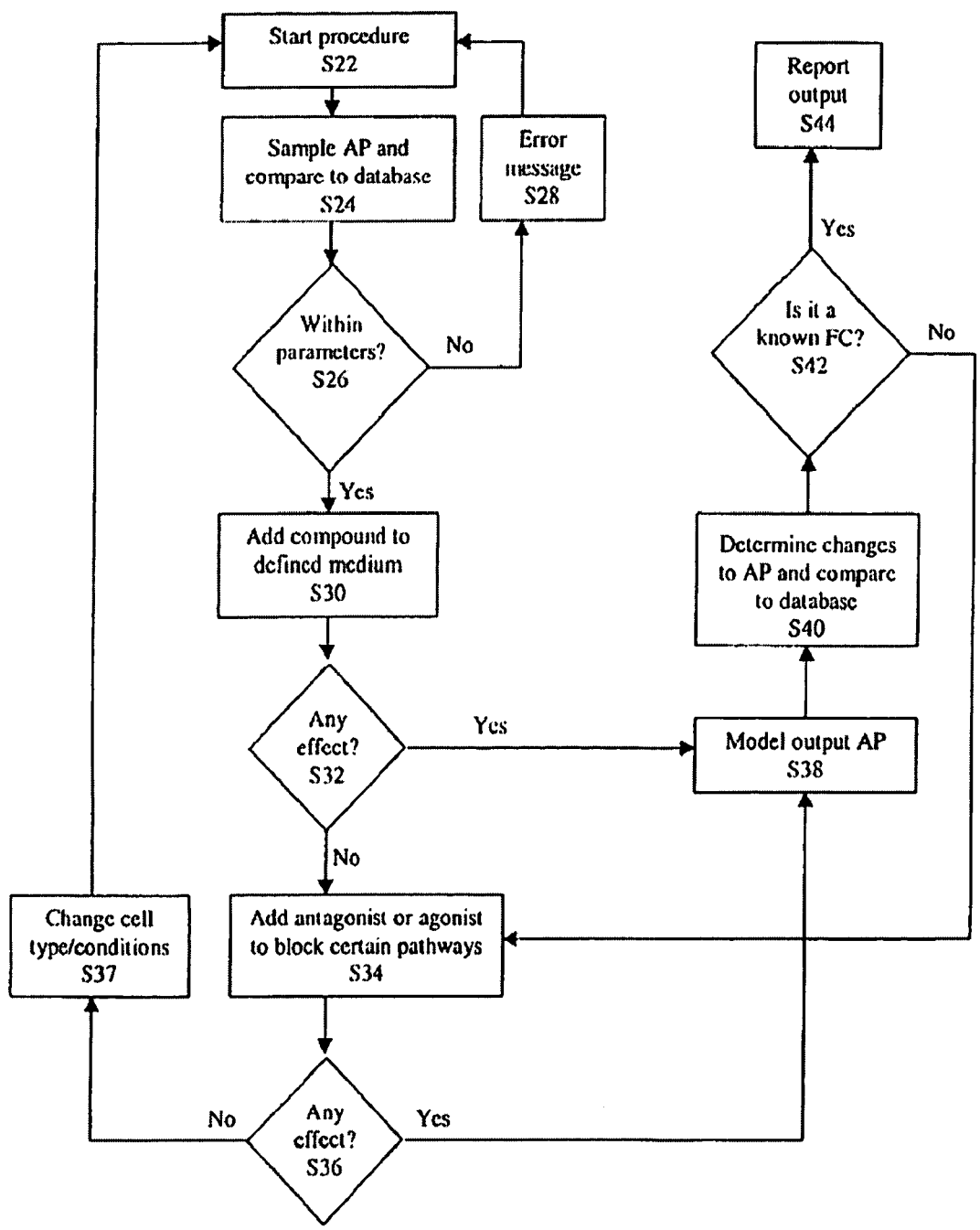

FIG. 10 provides a flow chart for a deconvolution algorithm.

Figure 11:
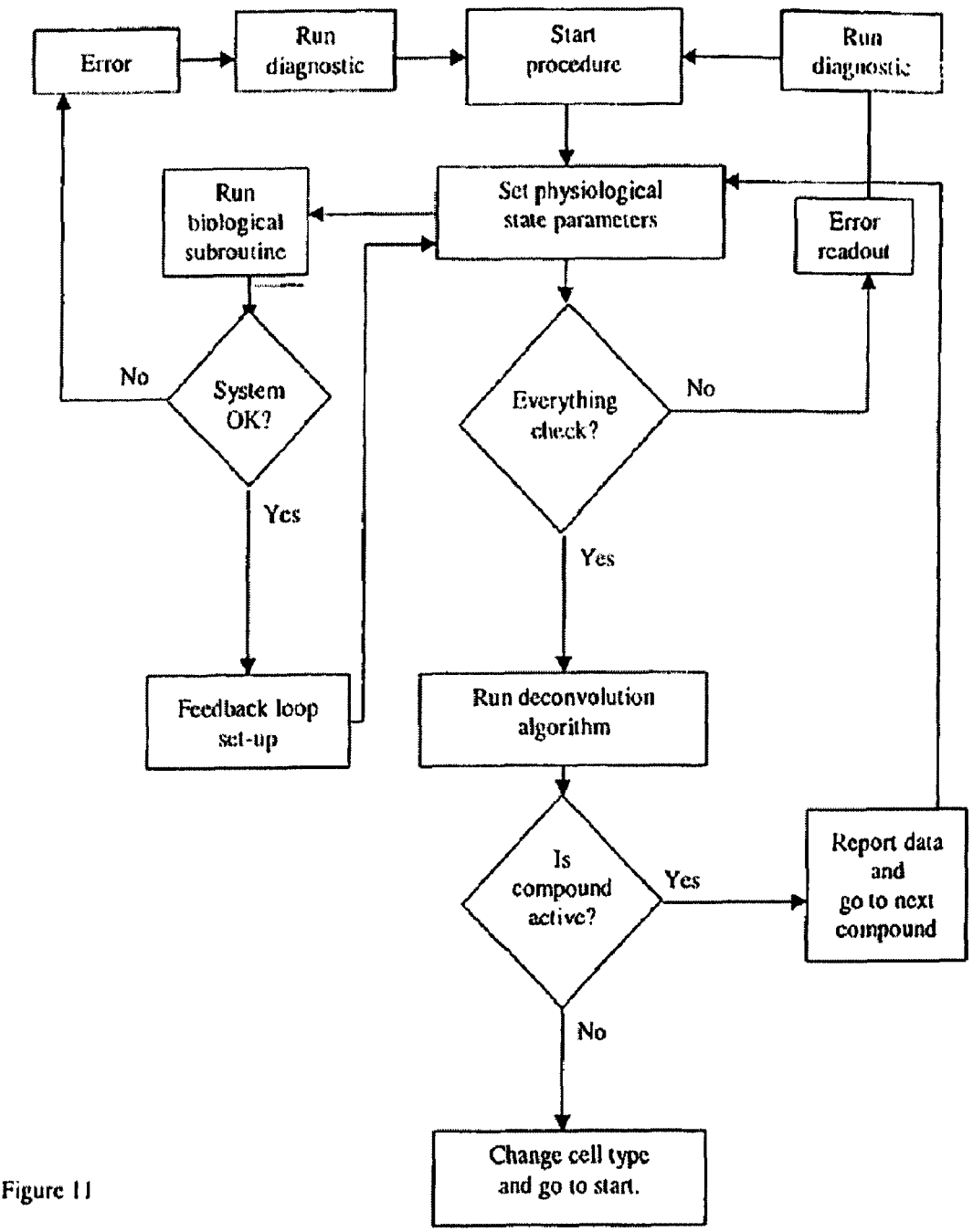

FIG. 11 provides a flow chart for a system or manipulation algorithm.

5. DETAILED DESCRIPTION OF THE PREFERRED EMBODIMENTS OF THE INVENTION

The invention has several components that function together for determining the effects of a test substance. One embodiment of the invention is a system comprising a solid state microelectrode; a cell culture which exhibits a electrical activity; and an intervening layer, which functions as a high impedance seal. The system is preferably accompanied by software capable of relating changes in the electrical activity of one or more cells of the cell culture to the physiological activity of the test substance (e.g., capable of deconvoluting an action potential). The term "test substance" is meant to cover broadly any substance whose effect on a biological system, such as a cell, one is attempting to determine. A test substance includes, but is not limited to, drugs, proteins, peptides, carbohydrates, nucleic acids, lipids, natural products, small molecules and the like. The "effects" of a test substance is likewise broadly construed and may include, but are not limited to, effects on ion flux, ion channel behavior, underlying cellular pathways, receptor function and response to agonists or antagonists, gene expression, cause/effect/progression of disease and the like.

FIG. 9 is a diagram showing the relationship of cells with microelectrodes, particularly in a carbon dioxide/molecular oxygen atmosphere. This is a microelectrode array with electrically active cells capable of producing action potentials—a rapid change of voltage across the membrane of a cell.

Referring to FIG. 9, a liquid or defined medium 4, such as an aqueous solution of nutrients, surrounds each cell 2. The defined medium 4 sustains the viability of each cell 2. The gases in the atmosphere are in equilibrium with dissolved gases in medium 4.

One or more system sensors 6 controls and monitors the parameters of the defined medium 4. These parameters include pH, temperature and osmolality, for example. Sensors 6 also regulate the nutrient inflow into the defined medium 4, as well as temperature in response to these changes.

In one embodiment, as shown in FIG. 9, a microelectrode 8, in an upper surface area, is formed with a modified sealed surface 10. Surface 10 is bound to and forms a high impedance seal over the microelectrode 8. Alternatively, and not shown, is an intervening layer that serves to anchor the cell 2. Cell 2 is capable of exhibiting electrical activity that can be monitored by the microelectrode 8.

Cells are generally separated by a second modified surface 12 (as shown), which is repulsive to cell adherence. Signals from each microelectrode 8 are transmitted by electrode lead wires 14 to a deconvolution algorithm and electronic control system 16. System 16 deciphers the role of several ion channels in the action potential of the cell 2.

The system algorithm 18 collects information from control system 16 and creates a database, which relates the properties of the action potential to different known agents that affect ion channels. The system algorithm 18 sends command signals to control system 16. The system algorithm 18 also sends commands to the biological system controller 20, which transmits updates and status information back to the system algorithm 18 and which also controls addition of compounds to test.

5.1. Solid State Microelectrode

In a particular embodiment, the invention comprises a solid state microelectrode that can be a flexible or a planar microelectrode. The flexible microelectrode array comprises a combination of electrodes and insulator readily adapted to bending, flexing, and twisting to permit positioning of the microelectrode on a variety of surfaces (or within certain internal structures). Hence, a microelectrode suitable for the present invention is one that can be placed on flat surfaces or on curved surfaces. The solid state microelectrode of the system can be a metal microelectrode. Moreover, the microelectrode can be a field effect transducer.

In another particular embodiment of the invention the microelectrode can further comprise an insulator and a conductor. Likewise, the conductor of the system can be constructed of gold, platinum, silver, copper, conductive glass, or combinations thereof, or any other suitable material. Moreover, the conductive glass of the system can comprise indium tin oxide. Similarly, the active surface of the microelectrode of the system can further comprise platinum black or iridium oxide. In one particular embodiment of the invention, the insulator surrounding the metal microelectrode of the system can be silicon, modified silicon dioxide, silicon nitride, silicon carbide, germanium, silica, gallium, arsenide, epoxy resin, polystyrene, polysulfone, alumina, silicone, fluoropolymer, polyester, acrylic copolymers, polylactate, or combinations thereof, or other suitable material.

5.2. A Layer Intervening between Microelectrode and Cell

In a particular embodiment of the invention, an intervening layer is established between the microelectrode/insulator array and the cellular component. The intervening layer can comprise a surface modifying agent. The surface modifying agent of the system can be a self-assembled monolayer. In still another embodiment of the system of the invention, the self-assembled monolayer is a silane. Cell anchorage molecules can further be used to form part of the intervening layer. In another embodiment of the system of the invention the cell anchorage molecules are antibodies, antigens, receptor ligands, receptors, lectins, carbohydrates, enzymes, enzyme inhibitors, biotin, avidin, streptavidin, cadherins, RGD-type peptides, integrins, cadherins, modified lipids, or combinations thereof.

In yet still another embodiment of a system of the invention the intervening layer comprises a high viscosity mixture. Suitable high viscosity mixtures include, but are not limited to, alcohols, ethers, esters, ketones, amides, glycols, amino acids, saccharides, carboxymethylsaccharides, carboxyethylsaccharides, aminosaccharides, acetylaminosaccharides, polymers thereof, or combinations thereof. Useful glycols can be polyethylene, polypropylene glycols and the like. In a yet further embodiment of the system of the invention the alcohols, ethers, esters, ketones, amides, glycols, amino acids, saccharides, carboxymethylsaccharides, carboxyethylsaccharides, aminosaccharides, acetylaminosaccharides, polymers (hereof, or combinations thereof are adherent to the monolayer.

The intervening layer of the present invention may further comprise an attractive layer, which increases cell anchorage, or may further comprises a repulsive layer, which decreases cell anchorage. Alternatively, the intervening layer can be a pattern of both attractive and repulsive layers which can confine a cell to a defined area.

5.3. Cells and Media for Cell Culture

The present invention makes use of electrically active cellular components and a variety of cell culture media. The cells of the cell culture are selected from electrically active cells, preferably those that give rise to measurable membrane or action potentials. The cell culture of the system can comprise a neuronal cell or a cardiac cell from a human, an animal, or an invertebrate. The cell culture can comprise primary cells or cells of a given cell line. Similarly, the neuronal cell of the system can be a hippocampal cell, a cortical neuron, a cerebellar neuron, a mid-brain neuron, a spinal cord neuron, or a peripheral neuron. Equally well, the cell culture of the system can comprises a stem cell, the progeny thereof, or a combination thereof. In one embodiment of the invention, the stem cell of the system can be exposed to a differentiating factor. Transformed (transfected) cells can also be used in the present cell culture. In a further embodiment of a system of the invention, the transfected cell comprises a cell harboring a test genomic or cDNA nucleotide sequence. In another embodiment the test nucleotide sequence can be any gene sequence provided in the GENBANK and updates thereof. Moreover, the test nucleotide sequence can be any gene sequence provided in the Celera gene database, and updates thereof.

The cell culture can optionally be coated with a polymer. The polymer that coats the cell culture can be cellulose, methylcellulose and the like. Various media can be used in the cell culture of the present invention. A preferred medium is serum-free medium. However, useful media can have additives or nutrients to facilitate cell function or growth. The additive can include growth factors, vital factors, vitamins, trace elements, and attachment factors. The components of the cell culture can be manipulated. For example, certain substances can be added, supplemented, or removed depending on the physical or physiological conditions being mimicked by the cell culture. Hence, a nutritive material or a cell modulator can be deleted to provide stress to the cell culture. In another example, glucose can be partly or completely deleted from the medium. Glucose or some other carbohydrate can also be added. Additional information on cell culturing techniques can be found, for example, in Freshney. I. I. "Culture of Animal Cells: A Manual of Basic Techniques." $4^{th}$ Ed. Wiley, John & Sons. March 2000. The contents of this and all other references provided in this specification are incorporated by reference herein.

5.4. Deconvolution Algorithm

In a particular embodiment, the invention comprises at least one algorithm for deconvolution of the action potential. The deconvolution analysis determines the contribution of the several ion channels, ion pumps, and other sources of electrical activity in the formation of the action potential or action potential train. A detector circuit, preferably a modified Fromherz circuit, can also comprise a system of the present invention.

Typically, a deconvolution algorithm is obtained by taking a basal signal from a system of the present invention; that is one records the signal (e.g., an action potential) from a base cell culture to which no test substance has been added. Such a basal signal is then stored for later comparison to a signal recorded from a system in which one of the system parameters has been altered or to which a test substance has been added. The differences in the recorded signals provides some measure of the effects of the altered parameter or added test substance. If certain known substances have known biological effects are used to obtain recorded signals, then one eventually can build up a library of changes to the electrical activity, which correlate to the types of biological effects being studied or which are desired. An algorithm is thus obtained from the collective information recorded and stored from the electrical changes induced by the known substances. This same deconvolution algorithm is then used to decipher if a test substance elicits the type of changes in electrical activity, which are indicative of the biological effects exerted by the known substances. Eventually, knowledge of various functional categories is built up, as illustrated in the Examples Section, below, which serve to indicate the likelihood that a given test substance exhibits a physiological effect that can be classified into one or more of such functional categories.

A more detailed description of the deconvolution algorithm and electronic control system 16 is provided in FIG. 10. The first step begins with a start procedure shown as block S22. The action potential is then sampled and compared to the database, as shown in block S24. The next step requires a determination of whether the action potential that is measured is within the limits of the parameters of the action potential stored in the database, as shown in block S26. If the measured action potential falls outside the limits of the parameters of the stored action potential, an error message is displayed (block S28), and the procedure returns to start.

On the other hand, if the measured action potential falls within the limits of the parameters of the stored action potential, then one or more desired compounds are added to the defined medium 4 (block S30). The next step requires a determination of whether the added compounds have caused a change in the action potential (block S32). If no changes are measured or noted, then the system adds an antagonist substance to block particular cellular pathways or an agonist substance to stimulate particular cellular pathways, as needed (block S34).

Here, again, a determination is required as to whether the added chemical compounds have caused a change in the action potential (block S36). If no changes are measured or noted, then the cell type or medium condition is changed, as at block S37, and the procedure is repeated.

On the other hand, if the chemical compounds added to the defined medium 4 have caused a change in the action potential, as at blocks S32 and S36, then a model output action potential is generated (block S38). The model output action potential is generally represented by at least three groups of ions. The first group is sodium, where flux flows from the outside of the cell to the inside. In the second group of ions, which is calcium, the flux also flows from the outside of the cell to the inside. In the third group, which is potassium, flux flows from the inside of the cell to the outside, and re-establishes the membrane potential.

In block S40, the deconvolution algorithm and electronic control system determines and/or measures the changes in the action potential of the model output, and compares the measured results to those stored in the database(s) (block S40). The next step requires a determination of whether the change in the model output action potential, corresponds to a known functional category of compounds (block S42).

If the change does not corresponds to a known functional category of compounds, then the system adds an antagonist substance to block particular cellular pathways or an agonist substance to stimulate particular cellular pathways, as needed, (block S34), and the steps proceed as described above.

On the contrary, if the change corresponds to a known functional compound category, then an output in the form of a report is presented (block S44).

5.5. Application of a System for Deconvolution on Test Substances

Accordingly, a method is provided, which comprises adding a test substance and analyzing the modified action potential using a deconvolution algorithm. See, FIG. 10. A deconvolving step, in a basic form, involves deciphering the relative contributions of ion fluxes attributable to different ion channels. In a higher form, the deconvolving step provides information on underlying processes, mechanisms, or pathways that contribute to the changes in the observed ion fluxes. In deconvolving the changes in electrical activity (e.g., changes in the action potential), a waveform, an action potential, or a transformation of same (e.g., a derivative, a frequency function and the like) may be viewed and analyzed. Conveniently, one can analyze the shape of a wave of an action potential. In a preferred embodiment of the present invention, the method is provided, which comprises the use of an optimized Hodgkin-Huxley waveform.

Other embodiments include temporal analysis of electrical activity, preferably, changes in membrane potential or action potential. Hence, the present invention contemplates the collection of data on, e.g. action potential, the one or more characteristics thereof, or one or more changes therein, followed by the determination from such data of which one or more ion channels, G-proteins, transporters, ion pumps, or combinations thereof are affected by the test substance.

5.6. A System for Functional Genomics Analysis

In a specific application of the present invention, a system is provided for determining one or more potential functions of an isolated nucleic acid, its expression product, or one or more active fragments of such nucleic acid or expression product. In particular, the system comprises a device that is optionally accompanied by software. The device comprises a solid state microelectrode and a cell culture comprising one or more cells that are capable of providing a measurable action potential that exhibits one or more perceptible characteristics and which cells have been either transfected with an isolated nucleic acid or exposed to its expression product. The optional accompanying software comprises data processing instructions capable of relating changes in the one or more characteristics exhibited by such action potential to one or more potential functions of such isolated nucleic acid, its expression product, or one or more active fragments of such nucleic acid or expression product. Preferably, the device further comprises an intervening layer that is acting as a high impedance seal and which is positioned between the microelectrode and the one or more cells of the cell culture.

Thus, recordings of the electrical signal from transfected cell cultures are recorded and compared to basal recordings. The differences in the recorded and basal electrical signals serve as an indication of the effects of the nucleic acid used to transform the cells of the cell culture. A high throughput assay for test substances that either mimic these effects or reverse them can then be undertaken. Alternatively, the effects of the nucleic acids can be compared to a database of known effects and underlying pathways to discern gene function.

5.7. System Algorithm

In one embodiment of the invention, the system comprises at least one algorithm that analyzes information on changes in ion channel function to determine which cellular processes are affected. See, FIG. 11.

Referring now to FIG. 11, a more detailed description of the system algorithm 18 is provided. This algorithm assures testing of 100 compounds or more. The first step begins with a start procedure shown as block S50. Physiological state parameters, such as polarization values, temperature, etc., are set, as in block S52. Here, an action potential is generated. The next step requires a determination of whether the set parameters fall within standard ranges (block S54). If set parameters fall outside these ranges, an error readout is generated (block S56), the system runs a diagnostic (block S58), and the procedure suns again. However, if a determination is made that the set parameters fall within the desired ranges, then the deconvolution algorithm is run (block S60).

At this juncture, a determination is required regarding whether the test compound has an affect on the action potential. If the test compound has substantially no effect on the action-potential, then the cell type and/or the medium conditions is/arc changed, as at block S64, and the procedure is repealed (i.e., return to start). If the compound has an affect on the action potential, a data report is output, as at S66, and the procedure is repeated through block S52 to test a subsequent or another compound.

It is important to recognize that concurrent with setting the physiological state parameters, as at block S52, the system algorithm is capable of running a biological subroutine, as at S68. Here, this subroutine is generally concerned with cell integrity, where a system check, as at S70, for example, can be performed on whether the cells are still viable, since they must be exposed to correct osmolarity and temperature. If the system check is negative, an error readout is output, as at S72, a diagnostic is run, as at S74, and the procedure returns to start.

However, if the system check is affirmative, a feedback loop is set-up, as at block S76.

Detection and Determination of Unknown Agents. Application of the system algorithm Manipulation algorithm) to the function of potential drugs and other agents, can result in determination of which cellular processes are affected by the agent. In a still more particular embodiment of the method of the invention, the deconvolution leads to information on pathways or functional categories affected in the cell.

Genomics Analysis. In a yet still more particular embodiment of the system, said accompanying software comprises instructions for manipulating one or more system parameters to alter one or more conditions of a given experiment, for interpreting the outcome of such manipulations, or for both.

One embodiment of the invention is a system for high throughput analysis comprising: a solid state microelectrode with an intervening layer comprising a surface modifying monolayer, which functions as a high impedance seal; a cell culture which exhibits a measurable action potential; and means for biological analysis, that is, deconvolution, of the action potential of the cell culture. The cell culture can be transfected with a gene, an isolated nucleic acid, a fragment of a nucleic acid, or combination thereof. In a yet further embodiment of the apparatus of the invention, the gene, isolated nucleic acid or fragment of a nucleic acid is from a human.

In still another embodiment of the apparatus of the invention, the algorithm comprises a feedback loop. The deconvolution and system algorithms are preferably stored on storage media, e.g., magnetic media (magnetic disk or tape) or optical media (CD-ROM).

5.8. Other Preferred Embodiments of the Invention

Another embodiment of the invention regards a kit for detecting an agent comprising a sensor comprising a cell culture comprising at least one cell which exhibits a measurable action potential, a solid state microelectrode, an intervening layer comprising a surface modifying monolayer which functions as a high impedance seal; and software capable of biological based deconvolution of the action potential; and a sampling device. In yet another embodiment of the kit of the invention the sampling device comprises an environmental sampling device, including, for example, an air pump.

Another embodiment of the invention regards a method of detecting an agent comprising: providing the kit, described above, and permitting an agent to interact with the sensor to detect the agent.

Another embodiment of the invention regards a kit for determining a gene function comprising a system comprising a solid state microelectrode, an intervening layer comprising a surface modifying monolayer which functions as a high impedance seal; software capable of biological analysis of an action potential; and an algorithm capable of elucidating a cellular pathway or receptor of interest to determine gene function; and a cell culture capable of hosting a transfection which exhibits a measurable action potential; at least one gene for transfection; and a transfection facilitator. In yet another embodiment of the kit of the invention, the transfection facilitator is an adenovirus or lipofectin.

Another embodiment of the invention is a computer readable medium including instructions being executed by a computer, the instructions instructing the computer to execute a method of high throughput analysis, the instructions comprising deconvolving an action potential of a cell culture. In yet another embodiment of the computer readable medium, the cell culture is adherent to a solid state microelectrode.

Another embodiment of the invention is a computer system for high throughput analysts, the system comprising: a processor; a computer program controlling operation of the processor, the program including instructions for causing the process to effect deconvolution of an action potential of a cell culture. In yet another embodiment of the computer system, the processor includes a network. In still another embodiment of the computer system the network includes an intranet, an internet, an extranet, or a virtual private network. In a further embodiment of the computer system, the processor is linked by standard wire or standard wireless means to the network.

In a further embodiment, another, separate, computer readable medium is provided which permits the parameters of the system to be changed and/or manipulated such that experimental conditions can be varied. In particular, the instructions encoded into a preferred computer readable medium are capable of customizing the system to provide desired outcomes on exposure of the system to one or more lest substances. Such a "system software" may make of other programs, including deconvolution software. It is important to note that while the present invention's deconvolution software preferably excludes spectral analysis, more specifically, a Fourier transformation, the present invention's system software may utilize such spectral analysis or Fourier transformation.

To further illustrate the present invention, the following examples are provided for consideration by the reader.

6. EXAMPLES

6.1. Use of Cardiac Myocytes and Spinal Cord Neurons

Figure 1A:
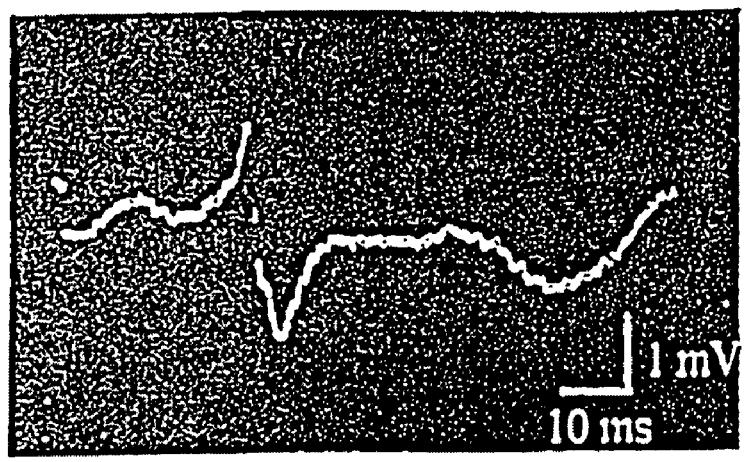
FIG. 1a illustrates a single extracellular action potential from spontaneously firing neonatal rat cardiac myocytes cultured for 7 days on a microelectrode array.
Figure 1B:
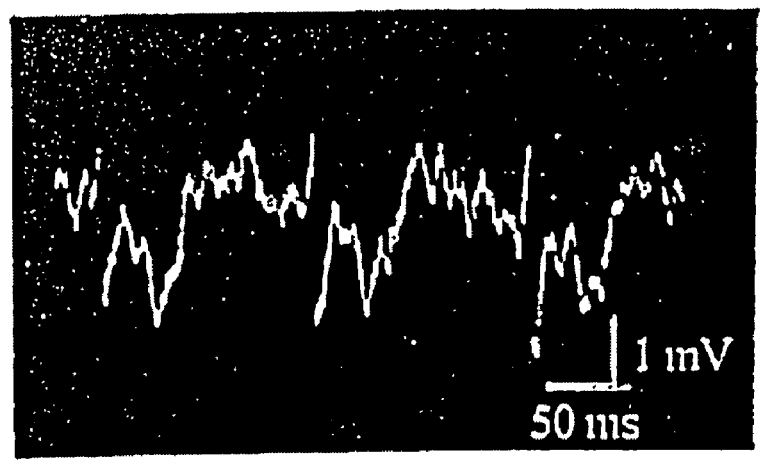
FIG. 1b illustrates a recording from the same microelectrode site but over a longer time span to demonstrate the pulsatility of the extracellular signal.
Figure 2B:
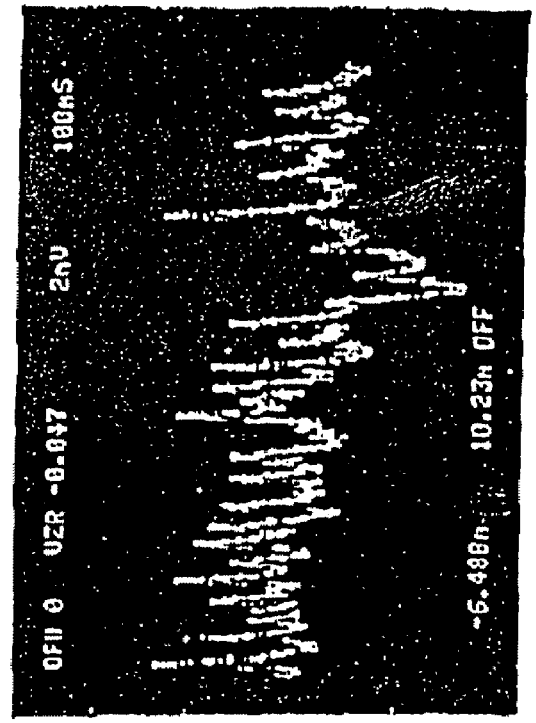
FIGS. 2A and 2B illustrates extracellular action potentials from spinal cord neurons on a microelectrode array. The cell firings are initiated by a depolarizing stimulus.
Figure 2A:
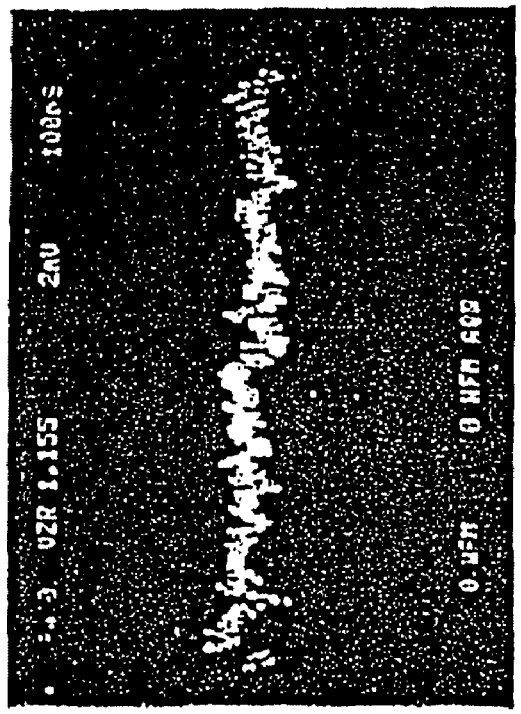
Figure 3:
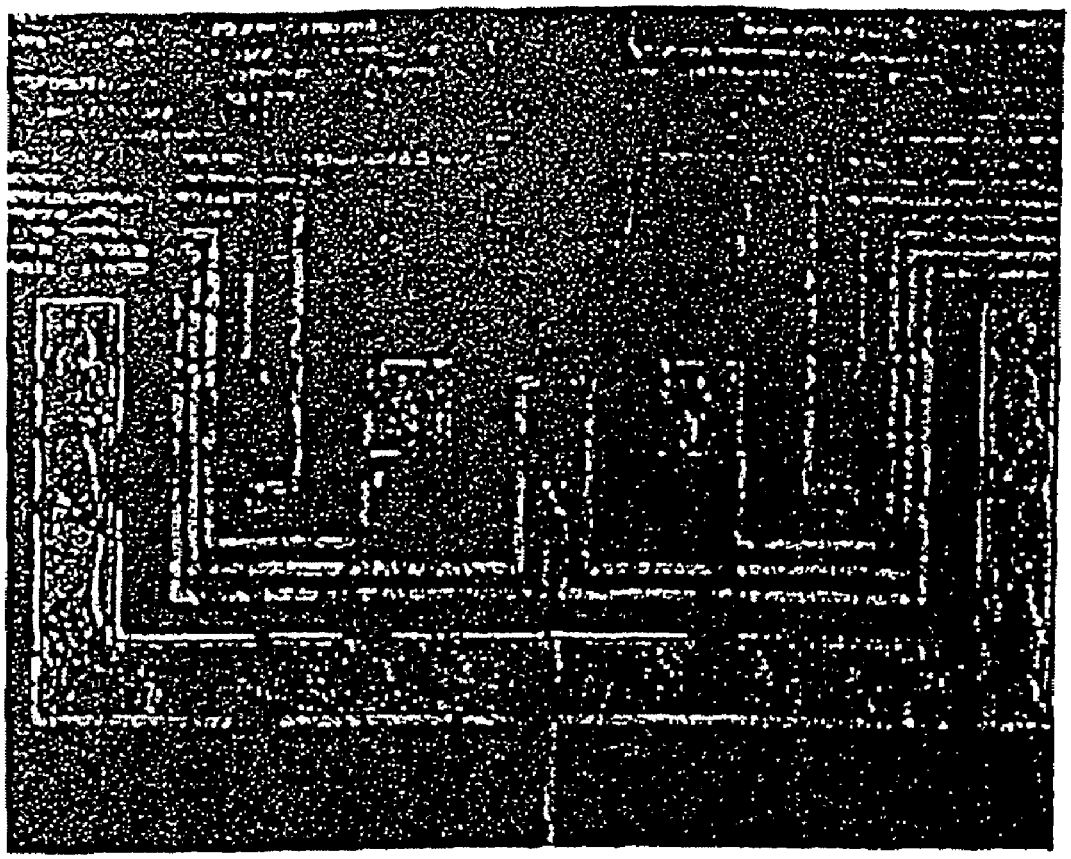
FIG. 3 illustrates an optical image of neurons cultured on a microelectrode array.

Templates for accurate spatial placement of a neuronal cell network is provided by the use of SAMs which permit application of a wide spectrum of circuit and fabrication technology to the detection of signals. Cold microelectrodes are used to measure signals from both cardiac myocytes (FIG. 1). Recordings are made at 37° C. The planar microelectrode array is platinized and coated with the cell permissive artificial substrate. Panel a illustrates a single action potential (AP) from a spontaneously firing monolayer. Panel b illustrates a recording from the same microelectrode site, but over a longer time spun, thereby demonstrating pulsatility of the extracellular signal. Signals from spinal cord neurons are illustrated in (FIG. 2). The recordings demonstrate cell firing initiated by depolarizing stimulus. Metal microelectrodes are used as substratum for neuronal cells in culture (FIG. 3). The neurons are grown on a modified $Si_3N_4$ coated microelectrode, and signals are recorded from Au microelectrodes in serum-free media. Thus cells are cultured in a defined media on a $Si_3N_4$ surface, the signals are recorded, processed and displayed by the electronic interface. The cell's activity on a microelectrode is attenuated by the introduction of a toxin to the in vitro environment which is experimental proof-of-concept for a neurotoxicity assay (Jung, D. R.; Cutlino, D. S.; Pancrazio. J. J.; P. Manos, P.; Custer, T.; Salhanoori, R. S.; Aloi, L. E.; Coulombe, M G.; Czarnaski, M. A.; Borkholdcr, D. A.; Kovacs, G. T. A.; Stenger, D. A.; Hickman, J. J. (1998), incorporated herein by reference, in its entirety. Cell-based sensor microelectrode array characterized by imaging x-ray photoelectron spectroscopy, scanning electron microscopy, impedance measurements, and extracellular recordings. *J. Vac. Sci. Technol. A,* 16(3), May/June. 1183-88.).

The difference in signal-to-noise between FIGS. 1 and 2 is due to the fact that the monolayer formed by the larger cardiac cells establishes a large seal resistance to the surrounding media by simply setting up a mechanical barrier to ion transport while the single neurons in the spinal cord culture are much smaller and isolated and the ions can more freely diffuse to the electrode surface. However, the results demonstrate that the signals produced by the mammalian cells are strong enough to be readily detected by the microelectrodes. As the seal resistance is increased the signal-to-noise approaches that achieved with glass micropipettes thereby allowing analysis of the AP waveforms from chip-based recordings.

6.2. Contribution of Ion Channels to Action Potentials

Another aspect of (his invention is the correlation of the shape of the action potential with the pathways stimulated by biological response modifiers. Neurons exhibit a modified action potential when acted upon by different pathogens and toxins that are then recorded by an electronic pickup. The NG108-15 (neuroblastoma×glioma) cell line, that exhibits stable electrical activity upon chemical stimulation is studied to show the effect of a wide variety of toxins on the action potential. The culture methods used and detailed electrophysiological characterization of this cell line are reported in Ma et al., 1998. A model system of an NG108-15 cell is illustrated in FIG. 4, which indicates the relationship of toxins from various "functional categories" to various pathways compiled from the literature ((Becerril, B., Marangoni, S., Possani, L. D. (1997). Toxins and genes isolated from scorpions of the genus *Tityus*. *Toxicon* 35, 821-35.; Brazil, O. V. and Fontana, M. D. (1993). Toxins as tools in the study of sodium channel distribution in the muscle fibre membrane. *Toxicon* 31: 1085-98.; Cantiello. H. F. (1995). Role of the actin cytoskeleton on epithelial $Na^+$ channel regulation. *Kidney Int.* 48:970-84.; Cassola, A. C. and Afeche, S. C. (1996). Use of neurotoxins to study $Ca^{2+}$ channel functions, *Braz. J. Med. Biol. Res.* 29: 1759-63.; Catterall W A, Trainer V, Baden D G. Related Articles Molecular properties of the sodium channel: a receptor for multiple neurotoxins. Bull Soc Pathol Exot. 1992; 85(5 Pt 2):481-5.; Childers, S. R. and Deadwyler, S. A. (1996). Role of cyclic AMP in the actions of cannabinoid receptors. *Biochem. Pharmacol.* 52: 819-27.; Cowan, F. M., Shih, T. M., Lenz, D. E., Madsen, J. M., Broomfield, C. A. (1996). Hypothesis for synergistic toxicity of organophosphorus poisoning-induced cholinergic crisis and anaphylactoid reactions. *J. Appl. Toxicol.* 16: 25-33.; Dryer, S. E. (1994). $Na^{(+)}$-activated $K^+$ channels: a new family of large conductance ion channels. *Trends Neurosci.* 17: 155-60.; Faden, A. I. (1996). Neurotoxic versus neuroprotective actions of endogenous opioid peptides: implications for treatment of CNS injury. *Nida Res. Monogr.* 163: 318-30.; Fields T A, Casey P J. Related Articles Signalling functions and biochemical properties of pertussis toxin-resistant G-proteins. Biochem J. 1997 Feb. 1; 321 (Pt 3):561-71; Fozzard, H. A. and Lipkind, G. (1996). The guanidinium toxin binding site on the sodium channel. *Jpn. Heart J.* 37: 683-92.; Harvey. A. L. (1990). Presynaptic effects of toxins. *Int. Rev. Neurobiol.* 32: 201-39.; Hille. B. (1994). Modulation of ion-channel function by G-protein-coupled receptors. *Trends Neurosci.* 17: 923-42.; Holstege, C. P. Kirk. M., and Sidell, F. R. (1997). Chemical warfare. Nerve agent poisoning. *Crit. Care Clin.* 13: 923-42.; Janiszewski, L. (1990). The action of toxins on the voltage-gated sodium channel. *Pol. J. Pharm.* 42: 581-8.; Kallen, R. G., Cohen, S. A. and Barchi, R. L. (1993). Structure, function and expression of voltage-dependent sodium channels. *Mol. Neurobiol.* 7: 383-428.; Lewis, R. J. and Holmes, M. J. (1993). Origin and transfer of toxins involved in ciguatera. *Comp. Biochem. Physiol. C.* 106: 615-28.; Mori, Y. G. Mikala, G. Varadi, G., Kobayashi, T., Kosh, S. Wakamori, M. Schwartz, A. (1996). Molecular pharmacology of voltage-dependent calcium channels. *Jpn. J. Pharmacol.* 72: 83-109.; Narahashi, T., Frey, J. M., Ginsburg, K. S., and Roy, M. L. (1992). Sodium and GABA-activated channels as the targets of pyrethroids and cyclodienes. *Toxicol. Lett.* Narahashi, T., Roy, M. L., and Ginsburg, K. S. (1994). Recent advances in the study of mechanism of action of marine neurotoxins. *Neurotoxicology* 15: 545-54.; Nestler, E. J. Alreja, M., and Aghajanian, G. K. (1994). Molecular and cellular mechanisms of opiate action: studies in the rat locus coeruleus. *Brain Res. Bull.* 35: 521-8.; Norton, R. S. (1991). Structure and structure-function relationships of sea anemone proteins that interact with the sodium channel. *Toxicon* 29: 1051-84.; Pearson, H. A., Campbell, V., Berrow, N., Menon, J. A. and Dolphin, A. C. (1994). Modulation of voltage-dependent calcium channels in cultured neurons. *Ann. N.Y. Acad. Sci.* 747: 325-35.; Pfister, C., Bennett, N., Bruckert, F. Catty, P. Clerc, A., Pages, F. and Deterre, P. (1993). Interactions of a G-protein with its effector: transducin and cGMP phosphodiesterase in retinal rods. *Cell Signal* 5: 235-41.; Piek, T. (1990). Neurotoxins from venoms of the *Hymenoptera*—twenty-five years of research in Amsterdam. *Comp. Biochem. Physiol. C.* 96: 223-33.; Rizzo, M. A., Koesis, J. D., and Waxman, S. G. (1996). Mechanisms of paresthesiae, dysesthesiae, and hyperesthesiae: role of $Na^+$ channel heterogeneity. *Eur. Neurol.* 36: 3-12.; Rowan, E. G., and Harvey, A. L. (1996). Toxins affecting $K^+$ Braz. J. Med. Biol. Res. 29: 1765-80.; Savolainen K M, Hirvonen M R. Second messengers in cholinergic-induced convulsions and neuronal injury. Toxicol Lett. 1992 December; 64-65 Spec No: 437-45.; Schantz, E. J. and Johnson, E. A. (1992). Properties and use of botulinum toxin and other microbial neurotoxins in medicine. *Microbiol. Rev.* 56: 80-99.; Smith, B. A. (1990). Strychnine poisoning (published erratum appears in *J. Emerg. Med.* 1991, November-December; 9(6): 555). *J. Emerg. Med.* 8:321-5.; Solberg, Y. and Belkin, M. (1997). The role of excitoloxicity in organophosphorous nerve agents enetral poisoning. *Trends Pharmacol. Sci.* 18: 183-5.; Swift, A. E. and Smith, T. R. (1993). Ciguatera. *J. Toxicol. Clin. Toxicol.* 31: 1-29.; Uchitel, O. D. (1997). Toxins affecting calcium channels in neurons. Toxicon 35: 1161-91.; Van, H. H., Busker, R. W., Melchers, B. P., and Bruijnzeel. (1996). Pharmacological effects of oximes: how relevant are they? *Arch. Toxicol.* 70: 779-86.; Wu. M. (1997). Enhancement of immunotoxin activity using chemical and biological reagents. *Br. J. Cancer* 75: 1347-55.; Yoshida, S. (1994). Tetradotoxin-resistant sodium channels. *Cell Mol. Neurobiol.* 14: 227-44)). In FIG. 4, bold face indicate toxins that have been tested. These data are also represented in Table 1. The significance of these results is that not only obvious neuronal toxins such as tetrodotoxin (TTX) affected the AP but also many others not so obvious, such as ricin. Out of 14 functional categories (Table 1), six affect the AP, including agents that modulate cellular processes, signaling pathways, transcription, is indicated. All of the listed toxins except VX lead to a cessation of the action potential within 180 seconds. However, differences are noted on the way the action potential ceases which we have used to determine which pathway and ultimately which ion channel is primarily affected by a particular toxin. This is illustrated in FIG. 5 which shows the AP after the administration of paraoxin, a transport and binding protein; ricin a protein synthesis inhibitor; and cyanide an energy metabolism inhibitor. FIG. 5 shows (top) the loss of signal upon administration of 3 mM paraoxon that shows a slowdown of signal or change in phase, the depolarization at the membrane, and onset of blockage in <60 s, which wits not reversible after toxin washout. The stimulated action potential using intercellular recording (middle) shows the dramatic changes in action potential shape for the duration, amplitude (AMP), and after hyperpolarization potential (AHP). Thus, identification of the cellular pathway by detailed interpretation of the recorded signal forms the basis of diagnostic concept of the present invention for identifying electrophysiological data and relating them to "cellular function" categories using our deconvolution algorithms.

An action potential is altered or interrupted in different ways by different toxins corresponding to interruption of ion channels in a pathway specific manner. Comparison of APs following the administration of different biological response modifiers or agents on cells leads to the identification of pathways for further development of analysis algorithms. The pathway determination involves parameters such as the shape change in the AP, time to cessation of activity, frequency and amplitude changes, and other factors.

The analysis of action potential signals is a sensitive indicator of the biochemical pathway or functional category involved. The logic is that the effects of some classes of toxins is to change ion conductance parameters (e.g. magnitudes or lime constants) with resulting changes in the extracellularly recorded waveshapes and spike rates. Signals are recorded which are either reduced amplitude copies of the membrane potential (when the seal resistance is high) or of the derivative of the membrane potential (when the seal resistance is low). To illustrate an implementation of the concept simulations of the Hodgkin-Huxley model are created in which the time constant of the sodium channel is doubled, and in which the potassium channel time constant is increased by a factor of five. The simulated extracellular somatic waveforms are either the membrane potentials (FIG. 6-$a$) or their derivatives (FIG. 6-$b$). In FIG. 6 the largest peak is from a simulation in which the potassium channel time constant was lengthened by a factor of five—note the longer afterpotential. The smallest of the peaks results from increasing the sodium time constant by a factor of two. The remaining peak is the normal 'textbook' Hodgkin-Huxley simulation. The slowing of the sodium channel decreases the signal amplitude, widens its main peak, but does not affect the afterpotential. The slowing of the potassium channel slightly increases the fast sodium peak, lengthens that peak but not its derivative, significantly lengthens the afterpotential, and greatly reduces the spike rate under constant stimulation (the latter not shown). These results clearly indicate that the waveform shape is very sensitive to even small variations in the conductance. These simulations, combined with the toxin data indicate the direct connection between the receptor effecting the pathways, the ion channels and the AP shape. These data are the beginnings of a library that will be formed from testing known compounds or drugs in our system and cataloging the changes in AP shape. The deconvolution algorithm will utilize these libraries to identify the functional categories and pathways affected by unknown compounds or genes.

6.3. Cell Types Useful in the Invention

Any electrically active cell can be used as a diagnostic element. One of these could be a cell line. The NG-108-15 cell line, used is derived from a gliomaxneuroblastoma hybrid and has been shown to provide reproducible results. Most of the data has teen collected with this cell type and they have been shown to live two to three months in our defined culture system. The lifespan of the primary CNS cells in our defined or reproducible cell culture system is about a month. Primary cells, however, have the advantage of more closely approximate in vivo systems than tumor-derived cell lines. A solution that combines the favorable aspects of these two options is the utilization of clonal lines derived from CNS stem cells. Companies, such as NeuralStem and BioWhitaker, have developed stable cell lines of CNS neurons from stein cells and have transformed primary neuronal cells into cell lines.

The electrical characteristics of all of these cells can be monitored on the microelectrode arrays. In addition to the remarkable ability to maintain the stability of the intrinsic neuronal character through many cell divisions, CNS stem cells are remarkably plastic; that is, a single extracellular factor can shift the fate specifications of the cells into largely one cell type or another. Thus, having a stable long-lived cell phenotype in combination with novel and advanced surface chemistry for specific placement of cells on microelectrode arrays for signal transduction forms key components of the assay system. Since each individual cell becomes a unique assay element and as the cells are localized on individual microelectrodes on a chip, statistics are performed on a reproducible population of cells in response to the compound or protein being examined.

6.4. Patch Clamp and Solid State Microelectrode-Based Electrophysiology to Enable Cellular Category Elucidation Cellular function in relation to changes in the neuronal action potential after biochemical introduction is determined by using biochemical "triggers" that each activate a distinct pathway in the functional categories, described above. The system is established by reproducible changes in the shape of the action potential that varies with some of the genetic categories described in 6.4.1 Further support is provided in FIGS. 4-7. Moreover, a subset of the major categories based on sequence homologies in the model system, can determine two "triggers" for each pathway, monitor the AP in the presence of these compounds, and demonstrate unique AP signatures for the pathways. A simple system such as bacterium can define a simple genetic basis for the evaluation.

TABLE 1

Assessment of Bio-Agents on NG-108-15 Cells

| Compound | Effect | Concentration | Onset Time |
|---|---|---|---|
| I. Transport/Binding Proteins | | | |
| tetrodotoxin* | $Na^+$ channel | 100 nM | <60 sec. |
| brevetoxin* | $Na^+$ channel | 10 μM | <60 sec. |
| apamin* | $K_{Ca}$ "SK"-type channel | 10 μM | <60 sec. |
| quinine* | non-specific $K^+$ channel | 2 mM | <60 sec. |
| Charybdotoxin* | $K_{ca}$ "BK"-type channel | 10 μM | <60 sec. |
| VX | reversible attenuation | 10 μM | <240 sec . |
| Paraoxon | irreversible depolarization | 3 mM | <60 sec. |
| DFP | irreversible depolarization | 250 μM | <60 sec. |
| II. Cellular Processes | | | |
| verapamil* | L-type $Ca^{2+}$ channel | 0.5 μM | <60 sec. |
| nifedipine* | L-type $Ca^{2+}$ channel | 0.5 μM | <60 sec. |
| ω-conotoxin* | N-type $Ca^{2+}$ channel | 10 μM | <60 sec. |
| amiloride* | L-type $Ca^{2+}$ channel | 10 μM | <60 sec. |
| carbachol* | muscarinic receptor | 10 μM | <60 sec. |

TABLE 1-continued

Assessment of Bio-Agents on NG-108-15 Cells

| Compound | Effect | Concentration | Onset Time |
|---|---|---|---|
| III. Cell Envelope/Membrane | | | |
| Palytoxin | irreversible depolarization | 1 μM | <60 sec. |
| IV. Regulatory Function | | | |
| ouabain* | Na$^+$—Ca$^{2+}$ pump inhibition | 2 mM | <60 sec. |
| V. Translation | | | |
| Ricin | irreversible depolarization | 10 μM | <180 sec. |
| VI. Energy Metabolism | | | |
| Cyanide | reversible depolarization | 100 μM | <60 sec. |

*indicates compounds which inhibit repetitive firing.

6.4.1. Cellular Categories from Genetic Data

The genetic categories based on sequence homologies defined for bacteria, are used initially to provide subsets of function for analysis. Of the 14 genetic categories defined by Riley et al. (Riley, M. (1993) Functions of gene products of *Escherichia coli*. *Microbiol. Rev.* 57, 862-952.), we use as examples groups most relevant to cell regulation, although all 14 categories can be investigated with the methods of the invention. Six broad categories have been selected: (a) Energy Metabolism, (b) Amino acid biosynthesis, (c) Cellular processes (d) Fatty acid, phospholipid, and steroid Metabolism, (e) Transcriptional regulation and (f) Transport and binding proteins. The neurons or cardiac myocytes are monitored for changes in the AP by glass microelectrodes in an on-cell extracellular recording mode or by microelectrode arrays. Signals corresponding to changes in the membrane potential are deconvolved using the methods described above. Two cellular preparations are particularly useful in the invention. First, cultured NG-108-15 embryonic hippocampal neurons are used. Analysis of these data identify characteristics of each category. A second set of data are collected for cells localized on the microelectrode array. This design permits determination of action potential shape changes that are characteristic of these six broad classes of compounds and how cells on the microelectrode array respond to stimuli in comparison to the well established cultured cell model.

6.4.2. Experimental Design and Detailed Compound Selection Rationale

Studies are performed with each test compound or "trigger" to determine an effective concentration. Effective concentrations cause a physiological response without causing cell death, within 12 hours of the initial exposure. The studies are conducted 7 to 10 days after cell plating. Unless otherwise noted, cells in the Examples are cultured and maintained in serum free media containing 10 mM glucose as described previously (Schaffner, A., Barker, J. L., Stenger, D. A., and Hickman, J. (1995). Investigation of the factors necessary for growth of hippocampal neurons in a defined system. *J. Neurosci. Methods*, 62, 111-119), although other media formulations are known to those skilled in the art.

Extracellular clamp electrophysiology is used to monitor how the action potential changes when the hippocampal neurons are exposed to different biochemical "triggers". These changes are used to map certain landmark events that occur intracellularly that are also related to the electrical activity of the individual ion channels whose collective activity comprise the action potential. This information is used to generate first stage algorithms to deconvolute the shape of the action potential and relate it to the pathways or categories (see below for AP waveform analysis). Specific examples of trigger agents and regulatory categories follow. One skilled in the art will be able to use other agents not listed here based on these examples.

6.4.2.1. Energy Metabolism-2-deoxy-D-glucose (2-DG)

A number of studies using adult hippocampal AC1 neurons have shown that temporary block of glycolysis by 2-deoxy-D-glucose (2-DG) reversibly suppresses synaptic transmission in the CA1 region of hippocampal slices. When the neurons recover, a sustained potentiation of field excitatory postsynaptic potentials (EPSPs) is observed. Thus, 2-DG is a molecule capable both of directly affecting the action potential and of inducing changes in gene expression and protein synthesis based on its metabolic action to block glycolysis.

The media in the apparatus of the invention is supplemented 24 hours before the start of the signal collection by adding 5 mM ketone bodies supplied as 2:1 ratio of β-hydroxybutyrate: acetoacetate as an energy source. Initial 2-DG is added to provide a 10 mM concentration. Additional inhibitors of energy metabolism acting at different sites can equally be used, including malonate, a compound that blocks energy production in the tricarboxylic acid cycle through NADH generation and 2,4-dinitrophenol, an uncoupler of oxidative phosphorylation.

Additional triggers are glucose and fructose. Glucose is a broad function energy metabolite but yields effects on the action potential with concentration changes. Comparison of glucose effect with fructose effect on the action potential has implications for the pathways and for particular disease states including diabetes and hypoglycemia.

6.4.2.2. Amino Acid Biosynthesis—Amino-oxyacetate

Amino-oxyacetate is a well described inhibitor of transaminase activity, notably those reactions transaminating glutamate. Although it is possible to synthesize both glutamate and GABA without transaminase activity, significant alterations in nitrogen metabolism are produced by this inhibitor. Such alterations can lead to changes in gene expression as a compensation to the effects of this compound.

Amino-oxyacetate is used at 5 mM with the system of invention. [$^{15}$N]-glutamine labeled in the amine or amide N is included in small aliquots of cells and the recovery of $^{15}$N in glutamate, aspartate, GABA or alanine is monitored with gas chromatography/mass spectrometry of these amino acids to verify alteration of transamine activity. Transfer of $^{15}$N from the main N of glutamate to other amino acids is blocked by an inhibitor of transaminase. The effect of inhibition of protein synthesis on the $^{15}$N patterns is used to correlate the action potential characteristics with the degree of change in these pathways.

6.4.2.3. Cellular Processes:—Cholecystokinin (CCK)

CCK is co-localized with the inhibitory neurotransmitter GABA in interneurons of the hippocampus. CCK receptors are found in abundance in the hippocampus and are known to antagonize the excitatory effects of opiates. A recent report found that the sulfated octapeptide CCK-8S increased action potential frequency or generated inward currents in the majority of hippocampal interneurons (Miller K K. Hoffer A, Svoboda K R, Lupica C. R. Related Articles Cholecystokinin increases GABA release by inhibiting a resting K+ conductance in hippocampal interneurons. J Neurosci. 1997 Jul. 1; 17(13):4994-5003). As CCK is known to have a complex functions in the brain including a role in satiety and possibly a detrimental role in ischemic damage, this compound provides a classic receptor mediated peptide type hormone with direct and immediate effects on the action potential.

CCK-8S peptide is used in the invention at concentrations known to affect the actions of opiates. 100 nM. The effects of a protein phosphatase inhibitor, GTP γS (300 nM) and a protein kinase inhibitor, okadaic acid (100 nM) are investigated to further clarify the CCK-8 response. Moreover, other peptide hormones acting via receptors on the hippocampal membrane such as neuropeptide Y, vasoactive intestinal peptide, and transforming growth factor-β are used in the system of the invention.

6.4.2.4. Fatty Acid and Phospholipid Metabolism/Cholesterol Synthesis, HMG CoA Reductase Inhibitor: Lovastatin Neuronal cells synthesize cholesterol dc novo using acetyl CoA (Edmond et al. 1991). This pathway is highly regulated and the most important control step is at the enzyme HMG-CoA reductase. De novo lipogenesis and cholesterol synthesis are particularly important in late fetal life and the early post natal period. Messenger RNA for key enzymes in the cholesterol synthesis pathway including HMG-CoA reductase, farnesyl pyrophosphate synthase, and cholesterol 7 α-hydroxylase increase during this period. In addition, lipophilic HMG CoA reductase inhibitors such as lovastatin affect the nervous system in the areas of sleep and cognitive function. As cholesterol is an important component of the cell membrane alterations in the shape of the action potential may be related to changes in the capacity to synthesize cholesterol.

Lovastatin is included in the tissue culture medium of the invention at 10 μM, a concentration that blocks HMG CoA reductase in cultured cells. To further clarify efficacy of this compound in blocking cholesterol synthesis a stable isotope method is used to quantify the actions of lovastatin on cholesterol synthesis. Moreover, other cholesterol synthesis inhibitors such as 25-OH-cholesterol and other modulators of lipid metabolism, including the carnitine palmitoyl transferase inhibitor TGDA and the anti-tuberculosis agent isoniazid, are used in the system of the invention.

6.4.2.5. Transcriptional Regulation—Corticosteroids

The modulation of neuron excitability by corticosteroids especially in hippocampal subfield CA1 is well documented (Okuhara D Y, Beck S G. Related Articles Corticosteroids alter 5-hydroxytryptamine 1A receptor-effector pathway in hippocampal subfield CA3 pyramidal cells. J Pharmacol Exp Ther. 1998 March; 284(3): 1227-33). The hippocampus contains the highest density of mineralocorticoid and glucocorticoid receptors in the central nervous system. Corticosteroids regulate gene expression through the activation of nuclear mineralocorticoid and glucocorticoid receptors.

Corticosterone is used in the invention for testing ion balance as reflected in the electrical activity of the cells. Moreover, other steroids, including aldosterone, dexamethasone and RU38486 are used in the system of invention.

6.4.2.6. Transport and Binding Proteins—Cholinergic Agonists, Carbachol

Cholinergic input to the hippocampus from the medial septum plays a key role in modulating hippocampal activity and functions, including theta rhythm and spatial learning. Recently it has been found that the cholinergic agonist carbachol caused several reversible changes in the action potential recorded from CA1 pyramidal cells in hippocampal slices (Figenschou A, Hu G Y, Storm J F. Related Articles Cholinergic modulation of the action potential in rat hippocampal neurons. Eur J Neurosci. 1996 January; 8(1):211-9).

Carbachol, the cholinergic agonist, is used in the invention to probe the cholinergic receptor at 2 μM. Moreover, other cholinergic antagonists such as pilocarpin or atropine, and agonists such as acetylcholine or muscarine, and partial agonists such as pilocarpine are evaluated.

Ion channel blockers are used to modulate the action potential. TEA (e.g., tetraethylammonium bromide) is very specific for the potassium channel. Similarly, TTX (tetrodotoxin) is specific for the sodium channel. TTX can block the spontaneous electrical activity of neurons and is a reversible blocker. The TTX-induced blockade of the electrical activity can result in an altered gene expression pattern in the developing neuron. Agonists of L-type voltage sensitive calcium channels are used to block effects of TTX.

6.4.3. Elements of the Biological Component 6.4.3.1. Creatine a Defined System and Neuronal Characterization Hippocampal neurons derived from embryonic day 18 CNS stem cell neurons, other neuronal cells, cardiac myocytes and other cells with a measurable membrane potential change are useful in the invention. NG-108-15 cells hippocampal neurons have been extensively used as models in various neuronal culture systems. They express the necessary neurotransmitter receptors and ion channels critical for the purpose of this invention. Hippocampal neurons are terminally differentiated, non-dividing cells. CNS stem cells can be differentiated into a neuronal-like phenotype which will express several of the desired neurotransmitter receptors and ion channels.

The cells are cultured on homogeneous SAM surfaces. DETA has been reported to be the best artificial surface for short term (<1 month) hippocampal culture. (Schaffner. A., Barker, J. L., Stenger, D. A., and Hickman, J. (1995). Investigation of the factors necessary for growth of hippocampal neurons in a defined system. J. Neurosci. Methods, 62, 111-119.) B27-supplemented neurobasal medium is used for neuronal growth, and the cells are incubated in 5% carbon dioxide in air (v/v) to create a defined scrum-free system (Brewer G J, Torricelli J R, Evege E K, Price P J. Related Articles Optimized survival of hippocampal neurons in B27-supplemented Neurobasal, a new scrum-free medium combination. J Neurosci. Res. 1993 Aug. 1; 35(5):567-76). This serum-free system selects against glial cells. Medium is changed twice a week to insure healthy cultures.

The neurons in the apparatus of the invention are characterized morphologically, immunocytochemically, and by extracellular electrophysiological recordings to evaluate changes in the membrane potential. A poly-D-lysine (PL) standard is run for each analysis to evaluate the general health of the original cell suspension.

6.4.3.2. Characterization of Neuronal Morphology

The neurons in culture are characterized according to several criteria described below. Cell survival and morphological characterization is accomplished by photographing the culture dishes at 24 hours after plating. Cell survival is assessed by comparing the number of cells surviving at a given point relative to the initial number of cells. The following quantitative values are also measured.

6.4.3.3 Cell-to-Substrate Surface Contact Area

Contact area of well separated cells is measured by marking the cell boundaries on the image and calculating the enclosed areas. A more adhesive substratum results in flatter, more adherent cells and thus a larger area in contact with the substratum.

6.4.3.4. Extent of Aggregation

As a measure of migration and cell-cell adhesion, aggregation is evaluated by measuring the total surface occupied by clusters or ganglion-like structures where contact inhibition has been lost.

To analyze these data the an imaging program is used which allows (1) drawing boundaries around cell somas or aggregates to calculate area, or drawing a boundary just outside the cell soma to calculate intersections and determine the number of primary neurites, (2) drawing the frequency histograms, and (3) performing a chi-square analysis to determine whether distributions differ with different protocols. An analysis of variance is performed to determine if there are treatment differences as well as plate differences. This permits determination the number of replicates necessary to generate statistically meaningful results.

6.4.3.5. Immunocytochemistry: Identification of Glia in Culture

Cells are characterized immunocytochemically for neuron-specific antigens (neurofilament neuron-specific enolase, Tujl), an astrocyte-specific antigen (glial fibrillary acidic protein), and an oligodendrocyte-specific antigen (galactocerebroside).

6.4.3.6. Neurotransmitter Expression

Neurons are characterized with respect to neurotransmitter expression with commercially available antisera to the neurotransmitters GABA and glutamate. The immunocytochemistry experiments is performed at days 7 and 10 after plating.

6.4.4. Differentiating Gene Expression

For detecting changes in gene expression, the experimental protocol allows facile detection of differences in action potential resulting from changes in gene expression. Thus, five test conditions are routinely compared for each compound:

(a) Control
(b) pre-incubated for 3 hrs with cyclohexamide, a well described protein synthesis inhibitor;
(c) +test compound alone;
(d) pre-incubated for 3 hours+test compound; and
(c) pre-incubated for 3 hours+cyclohexamide+test compound This strategy distinguishes those responses to the test compound that are immediate and not likely to be related to changes in protein synthesis (by comparison of 1 and 3) versus those responses that requite protein synthesis (by comparison of 4 and 5), with consideration of any effect of cyclohexamide.

6.4.5. Glass Microelectrode Recording from Neurons

Extracellular recordings that mimic the conditions used for on-chip recording are applied to neuronal cells. Changes in the membrane potential in a "maxipatch" mode which is an on-cell patch where a gigaohm sea) is formed to keep the noise low and enough of the cell membrane is contacted to make the ion channels representative are performed. The recording solution is the same as the extracellular medium in order that the membrane experience as normal an environment as possible. The potential in the pipette, which approximates the membrane potential, is recorded (current clamp mode, with zero current). (The circuit formed by the membrane, amplifier, and seal impedances is modeled to correct for differences between the potential recorded by the pipette and the presumed true membrane potential). The neurons are induced to fire by the addition of 40 mM KCl in lieu of electrical depolarization of the membrane. $Mg^{2+}$ is added to the media before recording to inhibit synaptic transmission. The electrophysiological properties of hippocampal neurons at 7 days after plating and 10 days after plating are compared. Other time points are examined as necessary.

6.4.6. Deconvolution Analysis of Action Potential Peak Shapes

The general methods for AP detection and sorting have recently been reviewed. (Wheeler, B. C. (1999). "Real Time Techniques for Automatic Discrimination of Single Units", book chapter, in press, to *Methods for Neural Ensemble Recordings*, M. Nicolelis (editor), CRC Press.) Analysis, i.e., deconvolution, of action potentials is based on a complete suite of algorithms, including sorting by amplitude, template matching and principal components, as well as automated cluster cutting to aid in determining the number of distinct APs in a recording and their waveshapes; also included are algorithms for extracting various spike train features (e.g. spike rate, burst rate and burst duration); stimulus driven measures (e.g. peristimulus time histograms, input/output functions); and inter-neuron correlation measures (e.g. cross-correlograms, mutual information).

The signal processing is performed by recording and analyzing action potentials before, during and after treatment with the appropriate toxins at prescribed concentrations. In the first step the changes in waveshape—e.g. measures of width, height, spike rate—are described as functions of the "trigger," concentration, and the cellular category on which the toxin acts. A model is applied to estimate the seal resistance from the recorded waveform data to assist in the interpretation. Secondly, a Hodgkin-Huxley type model is applied using conductance mechanisms and data in the literature for hippocampal pyramidal neurons. The parameters of the model are optimized to fit the acquired waveforms and waveshape measures. In the third stage the uniqueness of the changes as indicators of altered membrane physiology is evaluated; for instance in the example simulations, primary peak width is a good indicator of changed potassium dynamics when the seal resistance is high, but not if it is low (conversely, afterpotential duration should be more useful when the seal resistance is low). In all cases, statistical evaluation is performed, estimating the sensitivity of the measure to changes in membrane physiology with reference to the irremovable variation—both with instrumentation noise and variation from cell to cell.

6.4.6.1. Effect of Potassium Channel Modulators

Solid state microelectrode arrays are prepared having 32 gold microelectrodes and leads accessed by means of 14 μm diameter vias through a 1 μm thick silicon nitride lop layer on a silicon base. The arrays are chemically cleaned prior to electroplating and again prior to substrate modification with silane monolayers. First, the arrays are rinsed with de-ionized water and then with high purity liquid chromatography (HPLC) grade acetone. Then, each array is soaked in hexane for five minutes and then rinsed three times in acetone. Following these latter steps, the arrays are immersed in concentrated sulfuric acid: 30% (v/v) hydrogen peroxide (4:1 v/v) for two minutes and then rinsed five limes with HPLC grade water and three times with HPLC grade acetone. Microelectrodes are then electroplated with platinum black by standard procedures. The silane self-assembled monolayer is applied by reaction of the arrays for 15 minutes with 1% (v/v) of (aminoethylaminomethyl)-phenethyltrimethoxy silane in 94% (v/v) 1 mM acetic acid in anhydrous methanol and 5% water. A solution is prepared consisting of 1% (w/v) each of antibody to N-Cadherin, and, optionally, antibody to R-Cadherin, antibody to adult and embryonic pan-N-CAM, and antibody to neurite cell adhesion molecule L1 in 50 mM phosphate buffer, pH 7. This solution containing antibodies is incubated with the array for one hour in the absence or presence of 1 mM carbodiimide. The array is then rinsed once with HPLC grade water and once with Neurobasal medium. Hippocampal neurons are obtained by enzymatic digestion using papain (2 units/ml) from embryonic day 18-19 rat pups. Neurons are plated on substrates at a density of 1 to $1.5 \times 10^4$ cells/cm² and cultured in Neurobasal medium supplemented with 2% (v/v) B27, 0.5 mM glutamine, and 25 µM glutamate.

The impedance of each electrode is measured as described in Example 6.5.5. Each microelectrode with a suitably high impedance is used for further measurements. The action potential elicited by 2 µM carbacol is evaluated and compared to the action potentials elicited by 2 µM carbacol in the cells incubated in the presence of 1-10 µM apamin, 1-10 µM charybdotoxin, or 1-10 mM TEA. The contribution of potassium channels to the action potential is determined by the analysis methods described in 6.4.6., in particular analysis of changes in waveshape followed by application of a Hodgkin-Huxley model. The potassium channel function is further analyzed in terms of the concentration and type of blocker using the system algorithm (manipulation algorithm).

6.4.6.2. Analysis of Cyclic-AMP Regulated Pathways by their Modulation by Cholera Toxin Analysis of integrated or higher order pathways is accomplished by building on the analysis of ion channels as in 6.4.6.1., and similar analysis of sodium and calcium channels, in the higher order analysis (system analysis), several ion channels can be affected. For example, the effect of cholera toxin on the action potential is evaluated as follows. Cholera toxin is known to have a primary effect on the G-protein of adenylate cyclase, resulting in persistent activation of the enzyme and production of cyclic AMP. Using the system described in Example 6.4.6.1., the effect of graded doses of cholera toxin on the action potential of hippocampal neurons is evaluated. The changes in the action potential reflect, in part, changes in ion flux in the sodium, potassium, and calcium channels.

6.4.6.3. Analysis of Unknown Agents by Their Effect on Action Potentials

A collection of agents of unknown function derived from hunter snails, and other animals, from de novo synthesis, from medicinal plants, and elsewhere, is evaluated using the system described in Example 6.4.6.2. The effects of the agents on hippocampal action potentials are rapidly compared to the effects induced by toxins with known mechanisms of action. Thus, an agent is described as apamin-like, or cholera toxin-like, etc., based on the pathways and ion channels that are affected. Moreover, agents that affect multiple pathways can be analyzed in terms of the complex effects on the action potential.

6.4.6.4. Metabolic State as a Preexisting Condition for Further Analysis: Cross-Effects of Experimental Drugs with Fluctuations in Glucose and Insulin Metabolic states are important determinants of drug action and efficacy, yet are poorly modeled with current in vitro assays. Among the more significant metabolic states are those reflective of activity, such as exercise; eating or fasting; carbohydrate or fatty diet; and disease, such as diabetes. Physiological states corresponding to fasting and eating are modeled by reducing and increasing, respectively, glucose concentrations in the medium, concomitant with modulation in insulin concentrations. Similarly, ketoacidosis, hypoglycemia, hyperosmolarity, lactic acidosis, and other metabolic states can be modeled by one skilled in the art. The effects of normal and pathological states, including hypoglycemia and diabetes, on neuronal pathways are determined. Thereby, the rapid analysis of complex drug interactions at different metabolic states is possible.

After anchorage of hippocampal neurons or cardiac myocytes on solid state microelectrodes, the impedance is monitored to insure formation of a high impedance seal. KG is added to stimulate action potentials. Likewise, neurotransmitters or a shift in pH can be used elicit action potentials. The resultant action potentials are deconvolved by an algorithm for analysis of the biological response of the system. The culture medium bathing hippocampal neurons on the solid state microelectrode is then replaced, in a step-wise fashion, with Neurobasal medium with modified glucose concentrations, supplemented with 2% (v/v) B27, 0.5 mM glutamine and 25 µM glutamate. The medium is prepared with 25, 12.5, 6.25, 3.12, 1.56, 0.78, 0.39, and 0.20 mM glucose. Moreover, the cells are exposed to graded doses of insulin. Then the action potentials are again analyzed at each glucose and insulin concentration pair to elucidate the effects of glucose and insulin on ion channel function. KCl is used to initiate the action potentials. At a first phase of system analysis, the effect of glucose-insulin pairs on cellular processes is determined by comparison to the actions of known effectors. Then drugs can be screened or further evaluated. For example, acarbose, an alpha-glucosidase inhibitor sometimes used for reactive hypoglycemia and which reduces postprandial blood glucose and the insulin response is added to the hippocampal cultures. Similarly an entire combinatorial library of agents can be screened. Upon generation and recordation of action potentials a second phase analysis of the involvement of cellular processes is initiated. Thus the specific effects of the complex combination of acarbose with different levels of glucose and insulin are determined. Similarly, agents can be identified from a combinatorial library as effective in particular metabolic states.

By similar methods, the effect of clinical and experimental agents for treatment of diabetes are evaluated. The resulting information is particularly valuable for patients with multiple diseases or comorbidities who are subject to complex pharmaceutical interactions. For example, repaglinide is an agent that restores euglycemia by an action on ATP-dependent potassium channels in the beta cells of the pancreas. Graded doses of repaglinide are added to the system of the invention to rapidly analyze the effects of repaglinide on neuronal action potentials under a variety of metabolic states, including hypoglycemia, hyperglycemia, hypoinsulinemia, and hyperinsulinemia. Similarly one skilled in the art will understand that other agents can be tested using the system of the invention.

Hippocampal neurons anchored to the microelectrode are evaluated for formation of a high impedance seal. Action potentials are initiated by addition of KCl or carbacol, although other stimulators and neurotransmitters are equally useful. The resultant action potentials are analyzed to determine the relative involvement of specific ion channels. The culture medium bathing the neurons is varied so that the neurons are exposed to graded doses of glucose and insulin. In a first phase of system analysis, the effect of metabolic state on cellular processes is evaluated. Then the cells are exposed, at each glucose-insulin concentration pair, to repaglinide, to TGA, and to other neuromodulators of known function. In a second phase of system analysis, the complex interactions of repaglinide, insulin, and glucose are resolved to provide improved dosing regimens for clinical use. Similarly, a panel of other agents useful in disease treatment, including troglitazone and sulfonylurea is evaluated to select agents optimally effective for each metabolic or disease state.

6.4.6.5. Modification of the Viscosity of the Interface Layer

The viscosity of the interface layer can advantageously be increased in several ways. A moderate or high viscosity interface layer between cell and the silane layer on the microelectrode is associated with increased impedance of the seal.

In one method, a thickening agent is added to the bulk medium during attachment of the cells and subsequently the bulk solution is rinsed away with culture medium. Some of the agent is trapped between the cell and the surface of the microelectrode array chip. Thus in preparation for plating of hippocampal neurons, a culture medium containing between 0.1 to 10% (w/v) hydroxyethyl starch, preferably 1%, is used until the cells have attached and the high impedance seal is established.

In another method, a viscosity enhancer is bound to the silane layer on the microelectrode. Streptavidin is covalently linked to the amino groups of the silane by standard cross-linking chemistry. Then the microelectrode is exposed to biotin-conjugated antibody at a ratio of about 1:1 to about 1:0.01 (moles of antibody to moles of bound streptavidin) optimally about 1:0.1. After the antibody is bound (30 minutes at room temperature) to the streptavidin on the silane layer, the microelectrode array is exposed to a slight molar excess (over bound streptavidin) of biotin-conjugated viscosity agent, bis(polyoxyethylene bis[biotin], which has a molecular weight of about 20,000 Daltons. After a 30 minute incubation, excess reagent is rinsed away with HPLC water followed by a rinse with culture medium. Then cells (neuronal cells, NG-108 cells, or cardiac myocytes are equally effective) are seeded onto the microelectrode array. After the formation of a high impedance seal is verified by measurement on impedance, the hybrid bio-electrode or apparatus of the invention is ready for use.

6.4.6.6. Microelectrode Array Diagnostic Test: Cellular and Electrode Components Primary hippocampal neurons are grown under highly standardized conditions described above. The following cells are used: Young Control Neurons ("YC") isolated from fresh cadavers of adolescents or young adults (ages 15 to 30 years); Age-matched Control Neurons ("AC") isolated from fresh cadavers of elderly humans (60 to 80 years old); and Alzheimer's Disease Neurons ("AD") isolated from fresh cadavers of elderly humans with clinically diagnosed Alzheimer's Disease (60 to 80 years old). Neuroblastoma×glioma hybrids (eg. the NG-108-15 cell line) and cells transfected with the gene for amyloid precursor protein are equally useful.

Cells are seeded (approximately 5 cells per $mm^2$) onto microelectrode arrays, prepared as described above, in enriched culture medium and used when impedance measurements indicate establishment of a high impedance seal between at least one neuron and the substratum.

Electrophysiological measurements are performed at room temperature (21-23° C.) or, in other cases, as a function of temperature. Before recordings, culture medium is replaced with the following solution: 115 mM NaCl, 40 mM KCl, 2 mM $CaCl_2$, 1 mM $MgCl_2$, 10 mM HEPES (NaCl) pH=7.4, or in the alternative, fresh medium with selected neurotransmitter. Records are obtained using the instrumentation described below, linked to a personal computer for storage and analysis.

Multiple types of sodium, calcium, potassium channels within each cell and cell type are distinguished and recorded based on parameters of each channel, including conductance and current. Differences in ion channel properties between cells of different lineage are also recorded, in other measurements, the response of cells to a battery of neurotransmitter agonists is recorded, where the neurotransmitters include glutamate, carbachol, gamma amino butyric acid (GABA) and serotonin.

Specific but partial attenuation of ion channels with graded doses of toxins including TEA ($K^+$ channel), tetrodotoxin ($Na^+$ channel) and amiloride ($Ca^{2+}$ channel) are used in conjunction with deconvolution of the action potentials to determine the effect of model inhibitors. Additional agents and channel blockers are also used, including, but not limited to: strychnine, Red Tide toxin, verapamil, nifedipine, ω-conotoxin, ω-agatoxin, apamin, quinine, charybdotoxin, dendrotoxin, maitoxin, and $Ba^{2+}$.

6.4.6.7. TEA-$Ca^{2+}$ Diagnostic Test

Primary neuronal cells are grown as described above. Thirteen AD, ten AC, and six YC are used for the calcium-flux and calcium imaging experiments. Culture medium is replaced and washed three times with basal salt solution ("BSS") consisting of 140 mM NaCl, 5 mM KCl, 2.5 mM $CaCl_2$, 1.5 mM $MgCl_2$, 5 mM glucose, 10 mM HEPES (NaOH), pH 7.4. Nominally $Ca^{2+}$ free BSS is prepared as BSS without adding $CaCl_2$.

Fura-2 (acetyloxymethyl ester) (Fura-2AM) is purchased from Molecular Probes (Eugene, Oreg.) and stored as a 1 mM solution in dimethylsulfoxide. Fura-2AM is added to a final concentration of 2 μM and cells are incubated at room temperature (21-23° C.) for 60 minutes. After incubation, cells are washed at least three times with BSS at room temperature before [$Ca^{2+}$], determinations. Fluorescence is measured with a Hamamatsu ARGUS 50 imaging system (Hamamatsu Photonics, Japan) under the control of a personal computer (Hamamatsu imaging software package). Excitation at 340 nm and 380 nm is attenuated with neutral density filters. Fluorescent images are obtained with a 400 nm dichroic mirror and a 510 nm long-pass barrier filter. The objective lens is an X10 Nikon UV fluor. Fluorescence is measured within a uniformly illuminated fraction (¼) of the whole image.

The averaged $Ca^{2+}$ responses within 15×15 pixels in cytosolic and in nuclear cellular compartments obtained are quantified with ratios between emitted 510 nm fluorescence activated at 340 nm and fluorescence emitted at 510 nm with activation at 380 nm. These ratios are transformed to absolute values of [$Ca^{2+}$], after calibration based on the following equation:

$$R = R_{max} + (R_{min} - R_{max})/(1 + ([Ca^{2+}]/K_d)_b).$$

Here R denotes fluorescence intensity illuminated by 340 nm divided by fluorescence intensity illuminated by 380 nm (F340/F380), and $R_{max}$ and $R_{min}$ are the values of R when the concentration of calcium is at a maximum and a minimum (i.e., the maximum and minimum value measurable by the machine under the measuring conditions), respectively. $K_d$ is a dissociation constant of fura-2 for $Ca^{2+}$ and is determined at 240 nM. The value of b, which depends on the degree of asymmetry, is typically 1.2. TGA application is used to cause a minimum of 100% [$Ca^{+2}$], elevation in at least 18% of cells in every control cell. A response of 100% [$Ca^{+2}$], elevation in at least 10% of cells in a line is, therefore, a conservative criterion for a positive response.

The measurements of free intracellular calcium ion concentration ([$Ca^{2+}$],) is correlated to the $Ca^{2+}$ flux as measured by the deconvolved action potential, using specifically the current corresponding to calcium ion flux.

The neurons are depolarized by infusion of elevated external potassium in order to distinguish the elevation of intracellular $Ca^{2+}$ ([$Ca^{2+}$],) in YC compared to AC and AD neurons. The depolarization-induced [$Ca^{2+}$], elevation is eliminated by decreasing external calcium or by adding calcium channel blockers. The neurons are depolarization by addition of high $K^+$ to cause a marked [$Ca^{2+}$,] elevation in the various cell groups. The duration of the spike train of the calcium channel is correlated to the [$Ca^{2+}$], peak as measured by FURA-2 fluorescence and can be blocked if external calcium is lowered by substitution of "nominally $Ca^{2+}$ free" solution or 5 mM EGTA (estimated free $Ca^{2+}$=0.04 μM) or $Ca^{2+}$ channel blockers (0.1 mM LaCl$_3$, 10 mM CoCl$_2$, 10 mM NiCl$_2$, 10 mM CdCl$_2$ or 10 µM nifedipine) before stimulation.

The neurons are depolarized by addition of TEA to cause [Ca$^{2+}$], elevation, which is eliminated by decreasing external calcium or by adding calcium channel blockers. The AD neurons, can show [Ca$^{2+}$], elevation in elevated external potassium without [Ca$^{2+}$], response with addition of 100 mM TEA. Moreover, the AC and YC cells can respond to TEA, even when the AD cells do not.

The application of 1 mM TEA is used to elevate [Ca$^{2+}$], in YC neurons. The application of 10 mM TEA is used to elevate [Ca$^{2+}$], in YC and AC neurons. Similarly application of 100 mM TEA is used to elevate [Ca$^{2+}$], in YC and AC neurons. Similarly, the absence of external calcium ion is used to reduce or eliminate the response.

TEA is used to induce [Ca$^{2+}$], elevations for coded samples that include Alzheimer's and control neurons. Measurements and analyses are conducted without the experimenter's knowledge of the cell identity. The results are recorded for comparison with the non-blind sample.

Alzheimer's neurons from familial and non-familial cases are further used to evaluate agents with possible ameliorative properties. For example, choline esterase inhibitors can be compared using the system of the invention. After evaluation of the action potentials in YC, AC, and AD neurons, including deconvolution of the waveforms and comparison with known ion channel inhibitors, graded doses of choline esterase inhibitors are added separately, including: 3-[1-(phenylmethyl)-4-piperidinyl]-1-(2,3,4,5-tetrahydro-1H-1-benzazepin-8-yl)-1-propanone fumarate, metrifonate, donepezil, tacrine, and rivastigmine. The resultant action potentials are analyzed by application of the system algorithm to determine absolute and relative effects on nerve function and calcium channel function.

6.4.6.8. Bombesin-Ca$^{2+}$ Diagnostic Test

Human hippocampal neurons described above are used according to the culture methods and electrophysiological methods described above. Bombesin is purchased from Calbiochem (San Diego, Calif.) and stored as a 1 mM solution in distilled water. Fura-2 (acetyloxymethyl ester), fura-2 (pentapotassium salt) and ω-conotoxin (ω-CgTX) GVIA are from Molecular Probes (Eugene, Oreg.). Fura-2 AM is stored as a 1 mM solution in dimethylsulfoxide; fura-2 pentapotassium salt is stored as a 6 mM solution in potassium acetate, and ω-CgTX is stored as a 100 µM solution in distilled water. All of the chemicals except for phenyloin are maintained at –20° C. and protected from light.

The cells are incubated with 2 µM fura-2 AM in BSS (described above) at room temperature (21-23° C.) for 60 min. After being washed at least three times with BSS, the cells are used for measurement of [Ca$^{2+}$], at room temperature. Cell fluorescence is measured as described above. Absolute calcium values and calcium fluxes are calculated as shown above.

Bombesin is added to the cells at a final concentration of 1 µM. Calcium mobilization levels are measured from –30 seconds to 150 seconds after bombesin treatment. The maximum difference in [Ca$^{2+}$], between AD cells and control cells is determined and correlated to the differences in calcium channel function.

Bombesin is used to stimulate IP$_3$-induced Ca$^{2+}$ release from intracellular storage sites in neurons from all groups and to cause a larger and more prolonged response in AD neurons. The relationship of this larger and prolonged response in AD cells to extracellular Ca$^{2+}$ is determined. On the other hand, the IP$_3$-mediated Ca$^{2+}$ responses in AC and YC cells are followed by Ca$^{2+}$ entry and by the effects on the ion channels.

When this Ca$^{2+}$ entry is diminished by removal of extracellular Ca$^{2+}$, or blocking with inorganic Ca$^{2+}$ blockers, the bombesin-elicited Ca$^{2+}$ responses in control cells are returned to the basal level faster than in AD cells. Thus, this test is used to independently confirm the assessment made by the test above, based on potassium channel dysfunction See U.S. Pat. No. 5,976,816.

6.4.6.9. Effect of Rivastigmine and Nimodipine in a Model for Neurodegenerative Disease Action Potential Modulation in Neurons Overexpressing β-Amyloid The system of the invention is used to evaluate the efficacy of experimental agents in ameliorating the consequences or causes of neurodegenerative diseases. In particular, a model for Alzheimer's Disease is constructed by inducing the overexpression of β-amyloid in neurons. Sec U.S. Pat. No. 6,037,521 the disclosure of which is incorporated herein by reference, in its entirety. Models for other neurodegenerative diseases are known in the art and can equally well be used.

Hippocampal neurons transfected with the plasmids pfβ/NORβ, pβA/FADβ, pβA/Dβ, pβA/ΔNORβ and pβA/NLβ from U.S. Pat. No. 6,037,521 are separately plated onto microelectrode arrays and the adherence monitored by inverted optical microscopy and by an increase in the impedance at each microelectrode. The medium is modified to mimic the cerebrospinal fluid of Alzheimer's patients. After anchorage of the cells and development of a high impedance seal, the response of the normal and transfected cells to stimulation with non-specific neuronal stimulators, including KCl and a shift in pH, is measured. Moreover, the effects of specific neurotransmitters, including, but not limited to carbacol, glutamate, dopamine, norepinephrine, serotonin, and GABA are separately evaluated. The action potentials are deconvolved for the biological analysis of individual neurons. Following the deconvolution analysis, a first phase of system analysis (also known a manipulation algorithm) is directed toward the effect of the disease-associated media conditions and the transfection with disease-associated gene constructs. Agents of interest for the treatment of neurodegenerative disease are then applied to the neurons on the array. Acetylcholine esterase inhibitors, calcium channel blockers, and cellular redox inhibitors are of particular interest for Alzheimer's Disease, but other agents can equally well be evaluated. A key strength of the invention is the ability to quickly screen a large number of a wide variety of experimental and clinical agents. For example, control neuronal cells and neuronal cells transfected with pfβ/NORβ, pβA/FADβ, pβA/Dβ, pβA/ΔNORβ or pβA/NLβ are separately treated with graded doses of rivastigmine, an acetylcholine esterase inhibitor, or nimodipine, a calcium channel blocker. The relative effects of the agents on the deconvolved action potentials provides identification of the ion channel involvement as a function of the disease model, and are compared to a library of known responses to ion channel agonists, antagonists, and toxins. Then the resultant data are further analyzed in a second phase system algorithm (manipulation algorithm) to elucidate the effect of pfβ/NORβ, pβA/FADβ, pβA/Dβ, pβA/ΔNORβ and pβA/NLβ on energy metabolism, amino acid biosynthesis, cellular processes, lipid metabolism, regulation of transcription, and transport and binding proteins. The results are further quantified in terms of the relative effects of the agents on these major cellular systems. Thus, it is expected that some agents, although putatively acting by similar molecular pathways, can have differential effects that are reflected in the action potential and which correspond to differences in clinical efficacy and potency.

6.4.6.10. Measurement of Cell Surface Receptor Activation and Intracellular Signaling Via Second-Messenger Responsive Elements Activation of cell surface receptors leads to a change in intracellular messenger concentrations which in turn modulates intracellular transcription factor activity. In neurons, an increase the intracellular concentration of the messenger ion calcium leads to the activation of the nuclear factors. An increase in calcium levels alone is sufficient to markedly increase transcription of a reporter gene such as δ-lactamase and to modulate the action potential.

Rat hippocampal neurons anchored to microelectrode arrays are transiently cotransfected in situ with two plasmids. One plasmid contains the β-adrenergic receptor, which localizes at the cells' surface, under the transcriptional control of the strong and constitutively active cytomegalovirus (CMV) promoter. The other plasmid contains the bacterial RTEM β-lactamase gene from Escherichia coli modified for improved mammalian expression under the transcriptional control of a promoter containing a trimer of NFAT sites. The plasmids are introduced into cells using electroporation. $5 \times 10^6$ cells in 0.5 ml electroporation buffer are electroporated in the presence of 10 μg each of both plasmids using the Biorad Gene Pulser (250V, 960 μF, 16 μsec). Twenty-four hours after transfection, cells are incubated in the presence or absence of the β-adrenergic agonist isoproterenol (10 μmolar) and the stimulation continued for 5 hours until desensitization of the response occurs. The action potentials resulting from stimulation with isoproterenol and during the gradual desensitization are analyzed to determine the role of ion channels. The data manipulation, or system algorithm is then applied to evaluate the contribution of key cell regulation systems.

6.4.7. Stem Cell Culture and Use

CNS stem cells are the natural founder cells which are present in the primordial and spinal cord structures during the normal fetal development. The CNS stem cell technology available from of a number of commercial companies including NeuralStem Biopharmaceuticals and Biowhittaker enables isolation, expansion, and differentiation of CNS stem cells in vitro. Thus, subpopulation of neurons found in vivo can now be produced in vitro from their founding precursor cells. The hallmarks of the technology are that the CNS stem cells can be isolated in large numbers ($>10^7$ cells per rat embryo brain), further expanded up to a billion-fold over a 30-day period in culture, and efficiently differentiated in vitro where up to 80% of the cells become neurons. In addition to their desirable property of stably maintaining intrinsic information through many cell divisions, the CNS stem cells are also remarkably plastic. Thus, exposure of the cells to single extracellular factors can shift the fate specification of the cells largely into one cell type or another. For example, platelet-derived growth factor (PDGF) increases neuronal differentiation from 50% to 90% of the cells. Thus hippocampal neurons and stem cells differentiated into neurons are useful in the invention. Moreover, genes are transfected into the neurons and/or stem cells by standard methods to provide a cellular construct for analysis of exogenous gene function.

6.5. The Microelectrode-Neuron Interface

The methodology and rationale for creating the surface modification protocols for the placement of the neuronal cell bodies and the creation of the high impedance seal are described in this section.

Electrode arrays consist of solid substrates on which patterns of conducting wires lead from the electrode sites to external connecting pads. Many compositions are suitable as substrate material. The substrates are often glass, which is preferred for use with biological (inverted) microscopes, although silicon substrates are sometimes used because of their compatibility with electronic processing and the potential for on-site amplification of signals. The conductors (e.g. gold, indium tin oxide, polysilicon) are coated with an insulator, typically a plastic (e.g. polyimide, polysiloxane), or a glass (e.g. silicon dioxide and/or silicon nitride). Holes, typically 5 or 10 μm in diameter, are etched into the insulator to define the electrode site. The electrode sites are often inlaid with a desired interface material (e.g. gold, platinum, iridium oxide titanium nitride) to improve recording and biocompatibility. In a preferred embodiment, the surface of the insulation and electrodes are silicon dioxide and gold, respectively, which can each be further modified chemically as necessary.

Metal microelectrodes are used as transducers for the signals generated by the neurons or cardiac myocytes. The detection mechanism and how it will affect circuit design is shown in FIG. 7. During the action potential, the $Na^+$ and $Ca^{2+}$ channels open and $Na^+$ and $Ca^{2+}$ ions are transported, into the cell, across the membrane. $Na^+$ and $Ca^{2+}$ influx causes membrane depolarization which, over the region of the cellular membrane in contact with the metal microelectrode, results in a capacitive discharge current, $I_C = C_{jm} \, dV_m/dt$ where $C_{jm}$ is the junction-membrane capacitance and $V_m$ is the membrane potential. The fluctuation in charge polarization on the insulator over the interface produces a voltage difference across the metal, which is then detected as a change in the charging current of the microelectrode. Some time later, the $K^+$ channels open and $K^+$ ions flow out of the cell, across the membrane, and a similar but opposite sign impulse is imparted to the electrode.

A suitable circuit model of the detector system is shown in FIG. 8. The circuit is essentially that shown by Fromherz et al. (Wheeler, B. C. (1999). "Real Time Techniques for Automatic Discrimination of Single Units", book chapter, in press, to Methods for Neural Ensemble Recordings, M. Nicolelis (editor), CRC Press.) with the exception that we represent the electrode as an equivalent capacitance and the external amplifier as an ideal, discrete device. The membrane voltage. $V_m$, is taken to be an idealized AC source in parallel with the membrane capacitance, $C_m$. Any voltage appearing across the membrane appears across this capacitance in parallel with the junction-membrane capacitance $C_{jm}$. The signal current is divided between the seal resistance $R_{seal}$ or coupling to the amplifier through the electrode capacitance $C_{elec}$. One embodiment of the instant invention is the high impedance seal prepared using surface chemistry and optimized to minimize the current through the seal. Alternatively, if $R_{seal}$ is very large, then the membrane voltage appears at the amplifier input with little attenuation; if it is small then a smaller amplitude signal proportional to the derivative of the signal appears at the amplifier input.

The effect is illustrated by considering the voltage divisional the electrode (for an ideal amplifier)

$$Vo/Vm = KR_{seal}/\text{sqrt}[R_{seal}^2 + (1/jwC_{jm})^2]$$

where K is the amplifier gain, and w is the radian frequency of the signal component measured. For 10 μm square electrode pads fully covered by a membrane with specific membrane capacitance of 1 μF/cm2, $C_{jm}$ is approximately 1 pF; at 1 kHz, its impedance is 0.16 Gohm. If the seal resistance is much larger than 0.16 Gohm, the output equals the membrane potential; if it is much smaller, the output is the derivative of the membrane potential. If the amplifier is non-ideal and the seal resistance is high, there will be capacitive voltage division, between $C_{jm}$ (1 pF), $C_{elect}$ (approximately 1 nF), and the amplifier input capacitance (3 pF for the preamp by Multichannel Systems). Approximately 25% of the amplitude of the membrane voltage appears at the amplifier, while 75% appears across the membrane apposed to the electrode.

A major advantage of the system of the invention is dial it permits collection of data from up to 32 neurons or other cells, all exposed to identical conditions of temperature, culture medium, chemical stimulators and inhibitors. Thus, data of very high statistical quality can be obtained. Moreover, the artisan skilled in the art will realize that array can readily be prepared with more, or less, than 32 electrodes, by, for example, changing the total size of the array or the spacing between electrodes.

The simple model shown here illustrates that the recordable signal will vary from one that is proportional to membrane potential to one that is proportional to its derivative. The variation is a function of the seal resistance, the membrane properties, and the amplifier circuitry. This observation applies to both the preliminary work with patch electrodes as well as the patch quality coupling of the neurons to substrate electrodes. This model can be further refined for the generation of patch recordings from cells tethered to electrodes.

6.5.1. Construction and Characterization of the Neuron-Microelectrode Interface

A key component of this invention is the electrical characteristics of the neuron electrode interface. The biological/silicon interface is the result of the close contact between the glycocalyx of the neuron and the silicon/modified silicon dioxide surface. The neuron is a special case in that not only are the adhesion and viability of the cell crucial, but the ability to detect the electrical signals generated by the neuron with the silicon-based device is critical. These signals are capacitivity coupled to the surface so the signal falls as the distance between neuron membrane and electrode increases. These signals are detected by capacitivity coupling to a metal electrode. A key element of the invention is the optimal interaction of the neuron with the interface as well as detection of the signals in the solid state.

6.5.2. Construction of High Impedance Seals on Electrodes by Surface Modification The closer the neuronal membrane is to the metal microelectrode the stronger the signal that can be detected. Patch-clamp recording works so well because a gigaohm seal is created between the surface of the cell and the electrode tip using a combination of a pressure differential and surface interactions. This gigaohm seal almost eliminates the flow of ions from the surrounding media and allows membrane potentials and even small amplitude channel activity to be monitored in response to stimuli. A gigaohm seal is the most desirable result but the minimum necessary is that the noise is low enough compared to the signal to permit detailed analysis of the waveform. In the present invention tight binding of the neuronal cell surface to a artificially created surface over the microelectrodes is promoted to form a high resistance seal. A variety of biologically molecules that have strong interactions are used to create the seal, including, but not limited to antibodies that are used as neuronal markers. Suitable antibodies include, but are not limited to, the following antibodies or their equivalents, which are available from BD Biosciences.

TABLE 2

Neurobiology Antibodies

| Description | Clone |
|---|---|
| 14-3-3ε | 12 |
| Acetylcholine Receptor α | 26 |
| Acetylcholine Receptor β | 74 |
| Acetylcholinesterase | 46 |
| Adaptin α | 8 |
| Adaptin β | 74 |
| Adaptin γ | 88 |
| AF6 | 35 |
| Amphiphysin | 15 |
| AP180 | 34 |
| ApoE | 32 |
| Arc | 49 |
| β1-Calcium Channel | 44 |
| B56α | 23 |
| Bad | 32 |
| Bad | 48 |
| N-Cadherin | 32 |
| R-Cadherin | 48 |
| Clathrin Heavy Chain | 23 |
| Connexin-43 | 2 |
| Contactin | 41 |
| Dynamin | 41 |
| Dynamin II | 27 |
| GABA$^A$ Receptor (α1 Subunit) | Polyclonal |
| GABA$^B$ Receptor | Polyclonal |
| Glutamate Receptor (GluR1) | Polyclonal |
| Glutamate Receptor (GluR2 and GluR3) | Polyclonal |
| Glutamate Receptor (GluR2 and GluR4) | 3A11 |
| Glutamate Receptor (GluR2) | 6C4 |
| Glutamate Receptor (GluR2) | Polyclonal |
| Glutamate Receptor (GluR4) | Polyclonal |
| Glutamate Receptor (GluR5, GluR6, GluR7) | 4F5 |
| Glutamate Receptor (mGluR1α) | G209-488 |
| Glutamate Receptor (MGluR1α) | G209-2048 |
| Adult and Embryonic N-CAM (140 and 180 kD Epitopes) | 12F11 |
| Adult and Embryonic Pan N-CAM | N-CAM 13 |
| Embryonic N-CAM | 12F8 |
| Neurite Cell Adhesion Molecule L1-Related | 5G3 |
| NMDA (NR2A) | Polyclonal |
| NMDA (NR2B) | Polyclonal |
| NMDA (NR2C) | Polyclonal |
| NMDAR1 | 54.1 |
| NMDAR1 (N1) | Polyclonal |
| NMDAR1 (C1) | Polyclonal |
| NMDAR1 (C2) | Polyclona |
| NMDAR1(C2') | Polyclonal |
| (k) Opioid Receptor (N-terminus) | Polyclonal |
| (k) Opioid Receptor (N-terminus) | KAB |
| (μ) Opioid Receptor | Polyclonal |
| (μ) Opioid Receptor (N-terminus) | Polyclonal |
| (δ) Opioid Receptor | Polyclonal |
| Serotonin Receptor (5-HT2AR) | G186-I117 |
| Serotonin Receptor (5-HT2BR) | A72-1 |
| Serotonin Receptor (5-HT2CR) | A4-2 |

Similar antibodies are also readily available from other sources, or can be prepared by standard methods. They are linked to the thiols on the gold via standard crosslinking chemistry. These results are monitored by measuring the impedance at the metal microelectrodes. The protein buildup from the cells on the interface is monitored using surface analysis because excess buildup increases the distance between cell and metal microelectrode and thereby decreases signal strength.

6.5.3. Alternative Surfaces

Other surfaces and modifications are useful in segregating the cells, maintaining long term pattern fidelity and developing high resistance seals between cells and microelectrode chip. SAMs are used as templates for further derivatization by charge-induced condensations, heterobifunctional crosslinkers, or simple adsorption. In addition to antibodies, as above, oilier macromolecules including bovine serum albumin (USA), laminin, tenascin. Neural Cell Adhesion Molecule (NCAM), L1, basic Fibroblast Growth Factor (bFGF), and several glycosaminoglycans (GAGs) are suitable to form a tight seal with cells. The rationales for selecting these particular molecules are as follows:

(i) BSA: Albumin is a particularly prevalent protein in developing systems, and may play an important role in supporting the differentiation of embryonic cells. In addition, albumin has been shown to prevent the non-specific adsorption of other proteins. (Ligler, F. S., Calvert, J. M. Georger, J. H., Shriver-Lake, L. C, Bhatia, S. K., Bredchorst, R. U.S. Pat. No. 5,077,210 (1991).)

(ii) Laminin, tenascin, and NCAM: Laminin encourages neuronal growth. NCAM may induce proliferation of neurons. Tenascin has been shown to be repulsive to neurons and glia, and may be useful in keeping cells off of certain regions of patterned surfaces.

(iii) Growth factors (bFGF, BDNF): Growth factors are used as signals to cells to develop or differentiate, but their exact function is not clear. bFGF and BDNF promote neuronal survival.

(iv) GAGs: These polysaccharides represent the other major class of extracellular macromolecules (other than proteins) that make up the ECM. GAGs suitable for the invention include HS (heparan sulfate), chondroitin sulfate, and hyaluronic acid

6.5.4. Controlled Placement of Neurons on Metals Using Surface Chemistry

As described above, two different SAMs can segregate onto two different surfaces from the same solution. This result can also be achieved sequentially with certain materials and can, for example, be used to differentially modify the metal electrodes. The $Si_3N_4/SiO_2$ insulator is modified with a silane and then the Au microelectrode is modified with a SAM that promotes cell body adhesion or provides anchors for biological materials that will promote this interaction. The SAMs on Au are typically thiols. There is an extensive literature on their interaction with various electronic materials (Hickman, J. J., Ofer. D., Laibinis, P. E. Whitesides, G. M., and Wrighton, M. S. (1991). Molecular self-assembly of two-terminal, voltammetric microsensors with internal references. *Science* 252: 688) and on methods for further derivatization.

6.5.5. Impedance Measurements

Impedances are measured by the method shown in FIG. 4. (Jung, D. R.; Cuttino, D. S.; Pancrazio, J. J.; P. Manos, P.; Custer, T.; Sathanoori, R. S.; Aloi, L. E.; Coulombe, M G;. Czarnaski, M. A.; Bondholder, D. A.; Kovacs. G. T. A.; Stenger, D. A.; Hickman, J. J. (1998). Cell-based sensor microelectrode array characterized by imaging x-ray photoelectron spectroscopy, scanning electron microscopy, impedance measurements, and extracellular recordings. *J. Vac. Sci. Technol. A,* 16(3), May/June, 1183-88.) A 100 mV root mean squared (rms) signal is applied by a platinum wire in a 0.9% saline bath containing the microelectrode array. A lock-in amplifier (Model 5210 EC&G Princeton Applied Research) is used to monitor the resulting phase and amplitude of the potential at (his frequency (typically 1 kHz or 100 Hz) across a 1.01 M Ohm (precision resistor between the microelectrode and ground, yielding the real and imaginary parts of the microelectrode impedance, $Re(Z_{ma})=R_{ma}$ and $Im(Z_{ma})=X_{ma}=-j/(C_{ma})$.

6.5.6. Surface Characterization
6.5.5.1. Surface Characterization Prior to Cell Culture To relate the morphological and electrical properties of cultured neurons to changes in the conditions, each SAM-modified surface is characterized before each use by contact angle analysis, and XPS, if appropriate. Contact angle measurements are a way of quantitating the surface free energy of a modified surface. Characterizing surface hydrophobicity or hydrophilicity permits determination of relative hydrophobicity or functional group accessibility and is correlated to cell adhesion or phenotype XPS is a technique for the elemental analysis and characterization of the overlayers on surfaces that allows determination of efficiency of the modification techniques and also failure modes for establishing a good seal.

6.5.5.2. Surface Characterization after Cell Culture

The role or the surface in supporting neuronal growth is determined by measuring any reproducible changes in the amount, thickness, or distribution of macromolecules on the underlying SAMs after cell culture the emphasis is on the quantification of surface properties using quantitative XPS, imaging XPS, and biological assays as appropriate or necessary.

6.6. Device Fabrication and Testing

Planar electrode array recording of cultured neurons and muscle cells has been reported for nearly three decades since the work of Thomas et al. in 1972. The basic technology for recording is standard and well understood and, at present, there is ongoing and significant improvement in the commercial offerings of both arrays and supporting electronics. The standard instrumentation and data recording system in the invention is described here. Detailed descriptions of the commercially available platforms are well known to those skilled in the art.

The supporting electronic instrumentation consists of standard preamplifiers, standard amplifiers, standard filters, and a standard computer data acquisition interface. The system is capable of amplifying all channels simultaneously with adjustable gain and bandpass filtering so that signals in the range of a few microvolts to a few millivolts, and from a few Hz to 5000 Hz, can be recorded digitally. In addition, the system makes provision for either manual or entirely computer controlled electrical stimulation at individual electrode sites, including artifact rejection.

Action potentials (APs or spikes) are the primary signals recordable from the neurons cultured over the electrode arrays, in agreement with the experience of a number of investigators recording from cultured, dissociated neurons. (Wheeler, B C. & Brewer, G J 1994. *Multineuron patterning and recording*. In McKenna & Stenger (Eds.), *Enabling Technologies for Cultured Neural Networks* (pp. 167-185). Academic Press.) In addition, there may be occasional subthreshold events, in instances where there is excellent electrical coupling between neuron and electrode, and occasional field potential signals where the density of neurons is very high. The data recording of the invention focuses primarily on AP detection and analysis, while preserving the capability for logging and analyzing other types of signals. This will be considered in the development of the deconvolution algorithms.

6.6.1. Commercial Recording Systems

At present Plexon Inc. Dallas Tex. provides a product suitable for the invention capable of real-time sorting of spikes on 64 channels (and as many as 128); the software is designed to include automated cluster cutting as well as flexibility in the choice of spike sorting features. The system includes storage of detected waveforms to disk for purposes of reclassification of signals off-line. The product is supported by an excellent data analysis software package (Neuroexplorer) directed at analyzing spike train signals. The product line begins with connectors to electrode arrays and includes preamplifier and filtering.

The 64 channel MNAP (Multichannel Neuronal Acquisition Processor) includes high end personal computer, head stage stimulation/recording preamplifiers, input signal conditioning (SIG boards), A/D conversion (ADC boards) and digital signal processing (DSP boards), high speed host data communication (DCC boards), and output monitor (OUT board).

Multichannel Systems (Reutlingen, Germany) provides a product capable of continuous time acquisition of signals from 64 channels including a limited real-time ability to detect interesting events for subsequent data analysis. The data analysis software suggest a powerful product. The system includes electrode arrays and a compact stage pre-amplifier which greatly simplify recording logistics.

6.7. Protocol for High Impedance Throughput Analysis

The input-output relationships (spectral density and phase) of the extracellular clamp are derived from applying subthreshold amplitude sinusoidal voltage-clamp waveforms and measuring the output. In contrast, on a chip microelectrode, the ideal interface causes no signal attenuation or phase shift; however, the capacitive coupling of the interface imposes a low-pass filtering characteristic. Thus, the spectral density and phase relations provide quantitative measures of the interface characteristics for comparison among various SAM or SAM-modified surfaces.

6.8. Connection of the Apparatus of the Invention to a Computer

The apparatus of the invention may advantageously be connected to a computer or to a computer network.

One of ordinary skill in the art will recognize that with respect to the above-described computer network, the scope of the instant invention includes any suitable internet (lower case), i.e., any set of networks interconnected with devices, such as routers, that forward messages or fragments of messages between networks or intranets. Naturally, the Internet (upper case) is one of the largest examples of an internet.

To this end, it is to be understood that the elements of the service provider network, can be located in geographic proximity to one another in a substantially centralized processing environment, or can alternatively be arranged in a standard distributed processing environment so as to leverage resources, e.g., servers and storage devices, located at two or more sites.

In an alternative embodiment, the above-mentioned computer network may include a virtual private network (VPN), thereby taking advantage of existing PSTN infrastructure while providing a secure and private environment for information exchange regarding resource usage. Advantageously, data sent from the VPN is encrypted, thereby enhancing the privacy of customers. That is, because the VPN includes a tunneling protocol, the instant invention effectively uses the Internet as part of a private secure network. That is, the "tunnel" is the particular path that a given company message or file might travel through the Internet.

In another embodiment, the above-described computer network may alternatively include an extranet, wherein customers may securely exchange large volumes of resource usage data using a standard data exchange formal, for example, Electronic Data Interchange. To this extent, an extranet may enable customers to share news of common interest, for example, aggregated resource usage, exclusively with partner companies.

It should be understood dial although standard graphical user interface browsers have been discussed, standard text-only browsers, such as Lynx, may be used for UNIX shell and VMS users. Users of such text-only browsers may download comma-delimited ASCII files of, for example, their usage data.

Although the foregoing invention has been described in some detail by way of illustration and example for purposes of clarity of understanding, it will be readily apparent to those of ordinary skill in the art in light of the teachings of this invention that certain changes and modifications may be made thereto without deviating from the spirit or scope of the present invention. Hence, no limitations on the scope of the invention should be implied by the specific embodiments chosen to illustrate the invention.

What is claimed is:

1. A system for identifying one or more ion channels of a cell that may be affected by a test substance by deconvoluting a change in cell membrane potential, comprising:
   (a) a solid state microelectrode array;
   (b) a serum-free cell culture comprising one or more electrically active cells having a cell membrane including one or more ion channels, which cells are capable of providing a measurable action potential that exhibits changes in one more perceptible characteristics selected from after potential, time to cessation of activity, frequency, amplitude, shape, spike rate, or time constant in response to a test substance;
   (c) an intervening layer that is acting as a high impedance seal and which is positioned between said microelectrode and said one or more cells of said cell culture, and
   (d) accompanying deconvolution software with instructions that can be implemented by a computer to deconvolute changes in the action potential of the cells upon exposure to the test substance, wherein the deconvolution analysis does not include a spectral analysis that makes use of a Fourier transformation.

2. The system of claim 1, wherein the one or more characteristics exhibited by sad action potential is manifested in its waveform or a derivative thereof.

3. The system of claim 2, in which the one or more characteristics include at least one of time to cessation of activity, frequency, amplitude, or shape.

4. The system of claim 1, in which the instructions comprise data processing instructions capable of receiving input data comprising date on ion flux through ion channels selected from the group consisting of sodium channels, potassium channels, calcium channels, and combinations thereof.

5. The system of claim 1, in which the microelectrode is planar or flexible.

6. The system of claim 1, in which the microelectrode is a field effect transducer.

7. The system of claim 1, which further comprises an insulator layer surrounding the microelectrode selected from the group consisting of silicon, modified silicon dioxide, silicon nitride, silicon carbide, germanium, silica, gallium arsenide, epoxy resin, polystyrene, polysulfone, alumina, silicone, fluoropolymer, polyester, acrylic copolymers, polylactate, or combinations thereof.

8. The system of claim 1 in which said electrically active cell comprises a neuronal cell or a cardiac cell.

9. The system of claim 8, in which the neuronal cell is a hippocampal cell.

10. The system of claim 1, in which the cell culture comprises a stem cell, a transformed stem cell, their respective progeny, or a combination thereof.

11. The system of claim 1, in which said intervening layer comprises a self-assembling monolayers or monolayers.

12. The system of claim 11, in which the self-assembling monolayer comprises a silane, a thiol, isocyanide, polyelectrolyte or combinations thereof.

13. The system of claim 1, wherein the intervening layer further comprises cell anchorage molecules selected from the group consisting of antibodies, antigens, receptor ligands, receptors, lectins, carbohydrates, enzymes, enzyme inhibitors, biotin, avidin, streptavidin, RGD-type peptides, integrins, cadherins, modified lipids, and combinations thereof.

14. The system of claim 1, wherein the intervening layer further comprises a, high viscosity mixture comprising alcohols, ethers, esters, ketones, amides, glycols, amino acids, saccharides, carboxymethyl saccharides, carboxyethylsaccharides, aminosaccharides, acylaminosaccharides, polymers thereof, or combinations thereof.

15. The system of claim 1, in which one or more cells are transfected with endogenous or exogenous nucleic acid.

16. The system of claim 15, in which the nucleic acid comprises a nucleotide sequence associated with known function.

17. The system of claim 15, in which the nucleic acid comprises a nucleotide sequence associated with unknown function.

18. The system of claim 1, wherein the cell culture is coated with a polymer.

19. The system of claim 18, in which the polymer comprises cellulose, methyl cellulose, or dextran.

20. The system of claim 1, wherein a second layer is in contact with the electrically active cells and is attractive to cell adherence.

21. The system of claim 1, in which the test substance comprises a toxin, a drug, a pathogen, a neurotransmitter a nerve agent, or mixtures thereof.

22. The system of claim 1, in which the deconvolution of cell membrane potential includes deconvoluting the cell action potential or its derivative.

23. A computer readable storage medium encoding a program with instructions for execution by a computer in a system for identifying one or more ion channels of a cell that may be affected by a test substance by deconvoluting a change in cell membrane potential, said system comprising:
  (a) a solid state microelectrode array;
  (b) a serum-free cell culture comprising one or more electrically active cells having a cell membrane including one or more ion channels, which cells are capable of providing a measurable action potential that exhibits changes in one more perceptible characteristics selected from after potential, time to cessation of activity, frequency, amplitude, shape, spike rate, or time constant in response to a test substance;
  (c) an intervening layer that is acting as a high impedance seal and which is positioned between said microelectrode and said one or more cells of said cell culture, and
  (d) accompanying deconvolution software with instructions that can be implemented by a computer to deconvolute changes in the action potential of the cells upon exposure to the test substance, wherein the deconvolution analysis does not include a spectral analysis that makes use of a Fourier transformation.

24. A computer-readable storage medium of claim 23, in which one or more cells are transfected with endogenous or exogenous nucleic acid.

25. A computer-readable storage medium of claim 24, in which the nucleic acid comprises a nucleotide sequence associated with known function.

* * * * *